US008642046B2

(12) United States Patent
Camilli et al.

(10) Patent No.: US 8,642,046 B2
(45) Date of Patent: Feb. 4, 2014

(54) CHOLERA VACCINES

(75) Inventors: Andrew Camilli, Sharon, MA (US); Stefan Schild, Gratz (AT); Eric Jorge Nelson, Boston, MA (US)

(73) Assignee: Tufts University, Medford, MA (US)

(*) Notice: Subject to any disclaimer, the term of this patent is extended or adjusted under 35 U.S.C. 154(b) by 395 days.

(21) Appl. No.: 12/681,951

(22) PCT Filed: Oct. 9, 2008

(86) PCT No.: PCT/US2008/079292
§ 371 (c)(1), (2), (4) Date: Apr. 7, 2010

(87) PCT Pub. No.: WO2009/049013
PCT Pub. Date: Apr. 16, 2009

(65) Prior Publication Data

US 2010/0247566 A1 Sep. 30, 2010

Related U.S. Application Data

(60) Provisional application No. 60/978,727, filed on Oct. 9, 2007.

(51) Int. Cl.
*A61K 39/116* (2006.01)

(52) U.S. Cl.
USPC .................. 424/203.1; 424/261.1; 424/252.1

(58) Field of Classification Search
None
See application file for complete search history.

(56) References Cited

U.S. PATENT DOCUMENTS 7,125,718 B2 * 10/2006 Powell et al. ................. 435/458
7,915,218 B2 * 3/2011 Capecchi et al. .............. 514/2.8
2002/0028215 A1 * 3/2002 Kadurugamuwa et al. .......................... 424/234.1
2003/0105310 A1 * 6/2003 Ashkar ........................ 536/23.1
2004/0116665 A1 * 6/2004 Berthet et al. ................ 530/350
2004/0266003 A1 * 12/2004 Powell et al. ................. 435/455
2005/0176106 A1 8/2005 Ryan
2006/0134134 A1 * 6/2006 Perez Martin et al. .... 424/200.1
2006/0204520 A1 * 9/2006 Berthet et al. ............. 424/200.1
2007/0087019 A1 * 4/2007 Tucker et al. .............. 424/251.1
2007/0202342 A1 * 8/2007 Whiteford et al. ......... 428/425.5
2008/0138359 A1 * 6/2008 Steeghs et al. ........... 424/196.11
2008/0260769 A1 * 10/2008 Capecchi et al. .......... 424/192.1

FOREIGN PATENT DOCUMENTS

WO 01/89535 * 11/2001 ............. A61K 35/00

OTHER PUBLICATIONS

Tokuda, Hajime et al, FEBS vol. 264(1), pp. 10-12, May 1990, In vitro protein translation into inverted membrane vesicle perpared from *Vibrio alginolyticus* is stimulted by the electrochemical potential of Na+ in the presence of *Escherichia coli* SecA.*

Boardman, BK et al, J. Bacteriology, 2007, published ahead of print Dec. 22, 2006, vol. 189(5), pp. 1827-1835.*

(Continued)

*Primary Examiner* — Albert Navarro
*Assistant Examiner* — Ginny Portner
(74) *Attorney, Agent, or Firm* — Choate, Hall & Stewart, LLP

(57) ABSTRACT

The methods and compositions of the present invention are directed to a vaccine against *Vibrio cholerae* comprised of *V. cholerae* outer membrane vesicles (OMVs). Such vaccines are relatively stable, facilitating distribution. Inventive methods generally include administration of a vaccine against *Vibrio cholerae* by intranasal, intraperitoneal, oral or intragastric routes. Such vaccines confer immunity to the individual, and when administered to pregnant subjects, can be conferred to the offspring of individuals.

26 Claims, 10 Drawing Sheets

(56) References Cited

OTHER PUBLICATIONS

Dalseg et al., "Outer membrane vesicles from group B *Meningococci* are strongly immunogenic when given intranasally to mice", Vaccine, 17(19):2336-2345 (1999).

Rollenhagen et al., "Transcutaneous Immunization with Toxin-Coregulated Pilin A Induces Protective Immunity against *Vibrio cholerae* O1 El Tor Challenge in Mice", Infection and Immunity, 74(10):5834-5839 (2006).

International Search Report for PCT/US2008/079292, mailed Jul. 24, 2009.

International Preliminary Report on Patentability for PCT/US2008/079292, issued Apr. 13, 2010.

* cited by examiner

A.

B.

CHOLERA VACCINES

RELATED APPLICATION INFORMATION

This application is a national phase entry of international application serial number PCT/US08/079292, which claims the benefit of, and priority to, U.S. Provisional Patent Application 60/978,727 filed Oct. 9, 2007, the contents of each of which are hereby incorporated by reference in their entirety.

GOVERNMENT SUPPORT

This invention was made with government support under grant no. AI055058 awarded by the National Institutes of Health. The government has certain rights in the invention.

BACKGROUND

Cholera is a potentially life threatening disease endemic to many parts of the world. The disease manifests as an acute, diarrheal illness that, if untreated, can lead to severe dehydration and kidney failure. Cholera is caused by infection of the small intestine with the bacterium *Vibrio cholerae* (*V. cholerae*), usually via the oral-fecal route. Due in part to its extremely short incubation period (two hours to five days), devastating cholera outbreaks can arise very quickly.

Though cholera is often preventable and treatable, it is still responsible for many deaths due to lack of access to adequate medical facilities. The World Health Organization recommends that cholera vaccines be used in endemic areas. Existing cholera vaccines are too expensive and require complex logistics for distribution. Many countries where cholera is endemic, such as Bangladesh, cannot afford even the cheapest of the currently existing cholera vaccines. Due to instability of current vaccine formulations, a temperature-controlled system for distribution such as a cold chain is required. Such a requirement increases the cost of cholera vaccines. Thus, cholera vaccines often do not reach those who would benefit from such protection. Affordable, stable cholera vaccines that can be distributed more widely to cholera-endemic areas would be advantageous.

Outer membrane vesicles (OMVs) are shed from Gram-negative bacteria including *V. cholerae*. These vesicles are spherically shaped and average between 50 and 250 nm in diameter. They are comprised of a lipid bilayer containing integral or surface associated outer membrane (OM) proteins, phospholipids as well as lipopolysaccharide. and also enclose bacterial proteins that were present in the periplasmic space.

SUMMARY

The present invention provides vaccine compositions useful in providing protection from cholera, as well as, in some embodiments, other pathogens that cause diarrhea. The vaccine compositions comprise outer membrane vesicles (OMVs) of *V. cholerae* bacteria, a pathogen that causes cholera. Strains of *V. cholerae* from which OMVs can be derived include O1 serogroup (for example E7946 or O395), as well as O130 serogroup strains (for example Mo10). OMVs can also be derived from mutant strains of *V. cholerae*, such as strains that have been engineered to express heterologous gene products. For example, *V. cholerae* bacteria may be engineered to produce gene products derived from other diarrheal pathogens such as *Shigellae* (such as, for example, *Shigella dysenteriae, Shigella flexneri, Shigella boydii, Shigella sonnei*), *Salmonellae* (such as, for example, *S. enterica*), *Campylobacter jejuni, Helicobacter pylori*, rotavirus, *E. coli* (including subtypes such as enterotoxigenic *E. coli* (ETEC), enteroinvasive *E. coli* (EIEC), enteropathogenic *E. coli* (EPEC), enterohemorrhagic *E. coli* (EHEC), and enteroaggregative *E. coli* (EAggEC), and/or combinations thereof. OMVs prepared from such mutant strains may be loaded with the heterologous gene products, and vaccine compositions comprising such OMVs may be useful in providing protection from these other pathogens in addition to protection from *V. cholerae*.

Among the provided vaccine compositions are compositions suitable for intranasal administration and/or oral administration, including compositions that can be sprayed into the nose as a mist.

Also provided in the present invention are methods comprising administering such compositions. Administration of one or more of the provided compositions to an individual can confer immunity to that individual. In some embodiments of the invention, administration of one of the inventive compositions to an individual such as a pregnant female confers protective immunity to a child or to children of the individual.

In some embodiments of the invention, administration of a provided composition confers immunity to cholera. As discussed above, the compositions that can be administered in the provided methods may contain heterologous gene products. Thus, in some embodiments of the invention, the immunity that is conferred by the provided methods may be protective against other pathogens as well as those that cause cholera. Routes of administration include, among others, intranasal and oral.

Also provided in the present invention are methods of preparing the compositions described above. These methods comprise the steps of providing *V. cholerae* cells grown in culture, isolating OMVs from the supernatant of such cultures, and formulating a vaccine composition comprising such OMVs.

These and other objects, advantages and features of the present invention will become apparent to those of ordinary skill in the art having read the following detailed description of the preferred embodiments.

DEFINITIONS

Figure 1:
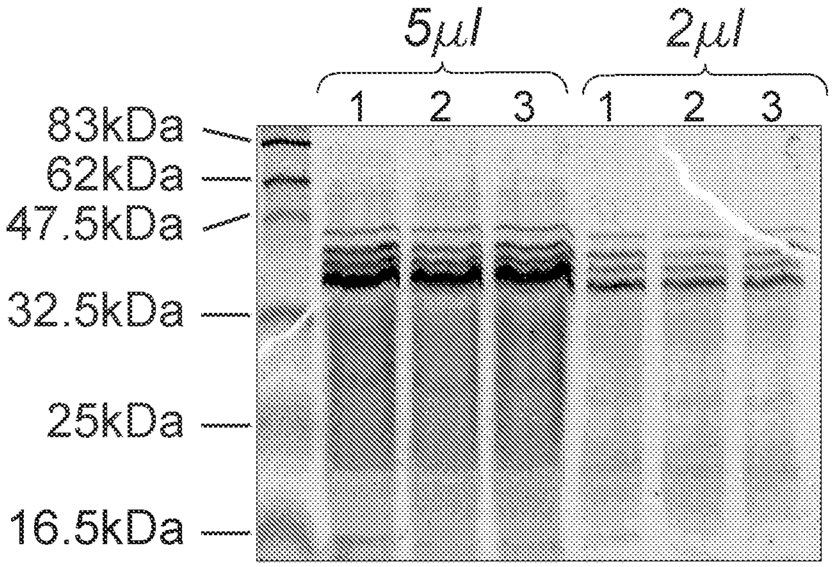
FIG. 1 depicts the results of an experiment examining the stability of outer membrane vesicles (OMVs) prepared from a wild type (wt) *V. cholerae* O1 serogroup strain (E7946). Proteins from (OMVs) were separated electrophoretically on an SDS-PAGE (sodium dodecyl sulfate polyacrylamide gel electrophoresis) gel. Lanes 1, 2, and 3 show protein from OMVs stored for 4 weeks at −80° C., −25° C., and 37° C. respectively. Molecular weight markers are shown in the leftmost lane. 5 and 2 microliters (indicated above the lanes) were electrophoretically separated on an SDS-PAGE gel and stained with IMPERIAL™ Protein Stain (Pierce).

As used herein, the terms "approximately" and "about" in reference to a number include numbers that fall within a range of 5% in either direction (greater than or less than) the number unless otherwise stated or otherwise evident from the context (except where such number would exceed 100% of a possible value.)

As used herein, the term "cold chain" refers to a temperature-controlled supply chain. A supply chain, also known as a supply network or a logistics network, is a coordinated system of organizations, people, activities, information and resources involved in moving a product or service from supplier to customer.

As used herein, the term "effective amount" refers to any amount of a compound or composition that is sufficient to fulfill its intended purpose(s), i.e., a desired biological or medicinal response in a tissue or subject. For example, in certain embodiments of the present invention, the purpose(s) may be: to elicit an immune response, to confer short-term immunity, and/or to confer long-term immunity to the subject treated with the compound or composition and/or to offspring of the subject treated with the compound or composition. As will be appreciated by those of ordinary skill in this art, the absolute amount of a particular agent that is effective may vary depending on such factors as the desired biological endpoint, the agent to be delivered, the target tissue, etc. Those of ordinary skill in the art will further understand that an "effective amount" may be administered in a single dose, or may be achieved by administration of multiple doses.

As used herein, the term "gene" has its meaning as understood in the art. In general, a gene may include gene regulatory sequences (e.g., promoters, enhancers, transcriptional terminators, ribosome binding sequences, etc.) and/or intron sequences, in addition to coding sequences (open reading frames). It will further be appreciated that definitions of "gene" include references to nucleic acids that do not encode proteins but rather encode functional RNA molecules such as small regulatory RNAs, tRNAs, or rRNAs. For the purpose of clarity it is noted that, as used in the present application, the term "gene" generally refers to a portion of a nucleic acid that encodes a protein, optionally encompassing regulatory sequence(s). This definition is not intended to exclude application of the term "gene" to non-protein coding expression units but rather to clarify that, in most cases, the term as used in this document refers to a nucleic acid that encodes a protein.

A "gene product" or "expression product" is, in general, an RNA transcribed from the gene (e.g., either pre- or post-processing) or a polypeptide or protein encoded by an RNA transcribed from the gene (e.g., either pre- or post-modification).

As used herein, the terms "foreign" and "heterologous" (used interchangeably), when used to describe a protein or other gene product, is used to mean derived from another species, or otherwise not normally present in a native species. As used herein, the definition of "heterologous" includes protein or gene products that are normally present in the native species, but have been modified, for example, by gene mutation or placed under the control of non-endogenous regulatory elements.

As used herein, the phrase "immune system" refers to a collection of mechanisms within an organism that protects against disease by identifying and killing pathogens and tumor cells. The immune system of an individual detects a wide variety of pathogenic and non-pathogenic agents, such as viruses, bacteria, parasites, etc., and functions by way of distinguishing such agents from the organism's own cells and tissues.

As used herein, the term "immunity" refers to a state of having sufficient biological defenses to avoid infection, disease, or other unwanted biological invasion, and is related to the functions of the immune system.

The terms "individual" and "subject" are used herein interchangeably. They refer to a human or another mammal (e.g., mouse, rat, rabbit, dog, cat, cattle, swine, sheep, horse, or primate) that can be afflicted with or is susceptible to a disease or disorder (e.g., cholera) but may or may not have the disease or disorder. In many embodiments, the subject is a human being. Unless otherwise stated, the terms "individual" and "subject" do not denote a particular age, and thus encompass adults, children, and newborns.

As used herein, the terms "intragastric" and "intragastrically" (abbreviated i.g.), when used to specify a route of administration, is used to mean into the stomach through the oral cavity and throat.

As used herein, the terms "intranasal" and "intranasally" (abbreviated i.n.), when used to specify a route of administration, is used to mean by way of nasal or sinus structures or both. In some embodiments of the invention, compositions are delivered intranasally by liquid droplet. In some embodiments of the invention, compositions are delivered intranasally by particle mist.

As used herein, the terms "intraperitoneal" and "intraperitoneally" (abbreviated i.p.), when used to specify a route of administration, is used to mean through the peritoneum, a thin transparent membrane that lines the abdominal (peritoneal) cavity and encloses the abdominal organs such as the stomach and intestines.

As used herein, the phrase "mucosal immune system" refers to a compartment of the immune system, comprising mucosa-associated lymphoid tissues (MALT) such as that of the gastrointestinal tract, genitourinary tract, nasal tissues, lung, other components of the respiratory tract, and/or breast. Mucosal immunity is immunity conferred by elements within the mucosal immune system, and gut-mediated immunity refers specifically to immunity conferred by immune system elements in the gastrointestinal tract. Cells that participate in gut-mediated immunity include antibody secreting cells, as well as M-cells, which are specialized for the uptake and transport of macromolecules and microorganisms.

As used herein, the term "mutant" refers to an individual, organism, strain of bacteria, or new genetic character arising or resulting from an instance of mutation. A mutation is a structural change within the DNA of a gene or chromosome of an organism resulting in the creation of a new character or trait not found in the wildtype. In certain embodiments of the invention, the mutant strain is modified such that it contains genetic material not normally present in the wild type strain of *V. cholerae*, such that bacteria of the strain produce heterologous proteins or RNA molecules arising from such genetic material. In some embodiments of the invention, the mutant strain produces heterologous gene products derived from pathogens other than *V. cholerae*, such *Shigellae, Salmonella enterica, Campylobacter jejuni, Helicobacter pylori*, certain strains of *E. coli* such as enterotoxigenic *E. coli* (ETEC), and rotavirus.

The terms "normal" and "healthy" are used herein interchangeably. They refer to an individual or group of individuals who are not diagnosed as having cholera.

As used herein, the term "outer membrane vesicle" (abbreviated as OMV and also known as OM vesicle and bleb), refers to vesicles secreted by Gram-negative bacteria. OMVs are discrete, closed blebs produced by growing cells. They appear spherical and typically have an average diameter of 50-250 nm depending on the strain of bacteria from which they are produced. OMVs comprise a bilayer membrane containing integral and surface associated outer membrane proteins, phospholipids, lipopolysaccharides (LPS), as well as periplasmic proteins enclosed in the OMV lipid bilayer. Proteins present in OMVs of pathogenic bacteria include, but are not limited to, adhesins, toxins, and immunomodulatory compounds. OMVs provide a means by which bacteria interact with other cells in their environment. For example, OMVs from pathogenic bacteria can participate in host-pathogenic interactions.

As used herein, the terms "oral" and "oral ingestion", when used to specify a route of administration, is used to mean by way of ingestion via the mouth.

As used herein, the term "pharmaceutical composition" is defined as a composition that comprises an effective amount of at least one active ingredient (e.g., an outer membrane protein or outer membrane vesicle), and at least one pharmaceutically acceptable carrier.

As used herein, the term "pharmaceutically acceptable carrier" refers to a carrier medium which does not interfere with the effectiveness of the biological activity of the active ingredient(s) and which is not excessively toxic to the host at the concentration at which it is administered. The term includes solvents, dispersion media, coatings, antibacterial and antifungal agents, isotonic agents, absorption delaying agents, and the like. The use of such media and agents for pharmaceutically active substances is well known in the art (see for example, "Remington's Pharmaceutical Sciences," E. W. Martin, 18th Ed., 1990, Mach Publishing Co." Easton, Pa., which is incorporated herein by reference in its entirety).

The terms "protein," "polypeptide," and "peptide" are used herein interchangeably, and refer to amino acid sequences of a variety of lengths, either in their neutral (uncharged) forms or as salts, and either unmodified or modified by glycosylation, side chain oxidation, or phosphorylation. In certain embodiments, the amino acid sequence is the full-length native protein. In other embodiments, the amino acid sequence is the full-length native protein. In other embodiments, the amino acid sequence is a smaller fragment of the full-length protein. In still other embodiments, the amino acid sequence is modified by additional substituents attached to the amino acid side chains, such as glycosyl units, lipids, or inorganic ions such as phosphates, as well as modifications relating to chemical conversion of the chains, such as oxidation of sulfhydryl groups. Thus, the term "protein" (or its equivalent terms) is intended to include the amino acid sequence of the full-length native protein, subject to those modifications that do not change its specific properties. In particular, the term "protein" encompasses protein isoforms, i.e., variants that are encoded by the same gene, but that differ in their pI, or MW, or both. Such isoforms can differ in their amino acid sequence (e.g., as a result of alternative splicing or limited proteolysis), or in the alternative, may arise from differential post-translational modification (e.g., glycosylation, acylation, or phosphorylation).

As used herein, the term "supernatant" refers to any liquid above non-soluble solids and/or precipitates. The solids may be separated from the liquid supernatant by methods such as, for example, settling, sedimentation, precipitation, membrane dialysis, centrifugation, etc.

As used herein, the term "vaccine" refers to a preparation that is used to establish immunity to a disease, thereby protecting a body from a disease, or reducing the chances of a body becoming affected by the disease. Vaccines can be preventative against the effects of a future infection or therapeutic (intended to reduce the severity of an infection or a disease, typically by assisting the immune system in fighting the infection or disease). In certain embodiments of the invention, a vaccine is a preparation that is used to establish immunity to a disease in the offspring of the individual to which the vaccine is delivered.

As used herein, the term "wild type" (abbreviated as "wt") refers to the genotype or phenotype that is found in nature or in the standard laboratory stock for a given organism. In certain embodiments of the invention, the wild type strains of *V. cholera* are the E7946 and O395 strains. E7946 is a clinical isolate from the 7th cholera pandemic, and is of the O1 serogroup, E1 Tor biotype and Ogawa serotype. O395 is a clinical isolate from the 6th pandemic and is of the O1 serogroup, classical biotype and Ogawa serotype.

DETAILED DESCRIPTION OF CERTAIN PREFERRED EMBODIMENTS

Compositions and methods of the present invention are directed toward vaccines protective against cholera, which is caused by the bacterial pathogen *V. cholerae*. Compositions provided herein generally comprise outer membrane vesicles (OMVs) obtained from *V. cholerae*. Certain methods provided herein generally comprise administering such OMV-containing compositions to an individual. Such methods can confer immunity to cholera in the individual or in the offspring of the individual who is administered a composition. Methods of preparing OMV-containing vaccines generally comprise steps of providing *V. cholerae* cells grown in culture, preparing OMVs from said *V. cholerae* cells, and formulating a vaccine composition comprising said OMVs.

A. Bacterial Strains

In some embodiments of the invention, the strain of *V. cholerae* is of the O1 serogroup. Included in the O1 serogroup are strains of the E1 Tor and classical biotypes, both of which contain Inaba, Ogawa and Hikojima serotypes. For example, in some embodiments of the invention, the *V. cholerae* strain is E7946 (ATCC 55056), a clinical isolate from the 7th cholera pandemic belonging to the O1 serogroup, having the E1 Tor biotype, and having the Ogawa serotype. In some embodiments of the invention, the *V. cholerae* strain is O395, a clinical isolate from the 6th cholera pandemic belonging to the O1 serogroup, having the classical biotype and having the Ogawa serotype.

In some embodiments of the invention, the strain of *V. cholerae* is of the O139 (Bengal) serogroup, implicated in outbreaks in Bangladesh and India in 1993. In some embodiments of the invention, the strain of *V. cholerae* is of a different serogroup, such as O37, O22, O11, etc. In some embodiments of the invention, the strain of *V. cholerae* is of a yet to be identified serogroup that has emerged as a cause of a cause of one or more cholera outbreaks.

In certain embodiments of the invention, the strain of *V. cholerae* is a mutant version of a known isolate. The mutation may have occurred naturally (such as that might occur by errors in replication machinery, or as a result of environmental insults to the bacterial genome), or it may be introduced experimentally. For example, it may be desirable to introduce one or more mutations into a naturally occurring strain of *V. cholerae* such that the strain produces a heterologous gene product, as discussed further herein.

In some embodiments, mutations are introduced to *V. cholerae* gene products. Such mutations may facilitate, for example, targeting of the *V. cholerae* gene products to certain organelles and/or cellular spaces (such as, for example, the periplasm and/or a membrane (e.g., outer membrane)), control of gene expression, increased loading of such gene products into OMVs, secretion of the gene product (which may, in some embodiments, facilitate attachment of the gene product to surfaces of OMVs) etc. For example, a constitutively expressed and/or inducible version of a gene encoding a protein may be introduced into the bacterial strain such that the protein accumulates to high amounts in the periplasm, which may, in turn, result in high amounts of such proteins in OMVs. For example, the gene encoding cholera toxin B subunit may be expressed constitutively and/or inducibly such that cholera toxin B subunit accumulates to high amounts in the periplasm and OMV. In some embodiments, sets of genes (such as, for example, operons) may be constitutively and/or inducibly expressed as described. The set of genes or operon may be, for example, an operon encoding a cholera toxoid comprising a wild type B subunit and an enzymatically inactive (mutant) A subunit.

Additionally or alternatively, one or more mutations may be introduced that increase the amount of OMVs produced by *V. cholerae*. Such mutations may, for example, facilitate mass production OMVs, alter protein content of OMVs, etc.

In some embodiments of the invention, a mutant strain is used in which the structure of lipopolysaccharides has been altered such that the lipopolysaccharides included in OMVs is less toxic. It may be desirable to use such mutants, for example, to allow administration by certain routes of administration that may result in exposure to vital organs such as the lungs.

A list of strains of *V. cholerae* of O1, O139, and other serogroups, can be found in the UniProt database entry for *V. cholerae* (taxon identifier 666) on the worldwide web at uniprot.org/taxononw/666, herein incorporated by reference in its entirety.

It will be understood by one of ordinary skill in the art that OMVs from any of these strains, and mutants of such strains, can potentially be used with provided methods and/or be components of provided vaccine compositions of the present disclosure.

B. Isolation of Outer Membrane Vesicles

In some embodiments of the invention, OMVs are isolated from the supernatant of liquid cultures of *V. cholerae* bacteria that are grown in nutrient-containing growth medium such as Luria-Bertani broth (LB). Bacterial cells can be pelleted from such liquid cultures by techniques such as centrifugation, and the OMV-containing supernatants collected. In some embodiments of the invention, OMVs are isolated from such supernatants by filtration, which can facilitate removal of remaining bacterial cells. In some embodiments of the invention, OMVs are separated from bacterial cells in liquid cultures by membrane dialysis. In some embodiments of the invention, OMVs are further purified from filtered supernatants by centrifugation. In some embodiments of the invention, OMVs are concentrated by a method such as centrifugation, such that the protein concentration of the OMV solution is of a desirable concentration. In some embodiments of the invention, the solution or supernatant containing OMVs is diluted in buffer or other liquids, such that the protein concentration of the OMV solution is of a desirable concentration. Isolated OMVs before and/or after dilution may be at sufficient concentrations for effective vaccine formulations.

In some embodiments of the invention, expression of proteins or other gene products is induced in bacteria before isolation of OMVs. For example, induction of gene expression can be achieved by adjusting the composition and temperature of the growth medium. For example, induction may be achieve by diluting a stationary phase liquid culture of bacteria in nutrient-containing broth that is mildly acidic (such as, for example, LB broth containing 0.5% tryptone, 0.25% yeast extract, 20.2% NaCl, pH 6.5) and growing the culture at 30° C. Induction of gene expression may also or additionally be achieved chemically, such as by adding IPTG (isopropyl beta-D-thiogalactoside) to the growth medium.

C. Vaccine Formulations

Vaccine compositions generally comprise isolated OMVs at a concentration such that an effective amount of OMVs may be delivered to the subject being vaccinated.

Vaccines may comprise OMVs resuspended in a solution or buffer (such as, for example, sterile distilled water, saline, phosphate-buffered saline, etc.). In some embodiments, vaccines contain no other components.

In some embodiments, vaccines comprise additional components. For example, protease inhibitor(s) and/or other substances may be included to stabilize OMVs.

Compositions may include proteins that may or may not be enclosed or embedded within OMVs. For example, purified cholera toxin B subunit and/or purified cholera toxoid (i.e., a catalytic mutant of cholera toxin, for example, a toxoid comprising a wild type cholera toxin B subunit and a enzymatically inactive mutant cholera toxin A subunit) may be included in the vaccine composition comprising OMVs.

Alternatively or additionally, adjuvants may be included in vaccine compositions. Adjuvants may, in certain embodiments, enhance production of antibodies against *V. cholerae* OMVs. Examples of suitable adjuvants include, but are not limited to, various oil formulations and/or emulsions such as stearyl tyrosine (see, for example, U.S. Pat. No. 4,258,029), muramyl dipeptide (also known as MDP, Ac-Mur-L-Ala-D), saponin, aluminum hydroxide, lymphatic cytokine, etc. Adjuvants that are particularly suitable for inducing mucosal immunity include, but are not limited to, cholera toxin B subunit, heat labile enterotoxin (KT) from *E. coli*, Emulsomes (Pharoms, LTF., Rehovot, Israel), etc.

Vaccines may be formulated for multiple immunizations, and an effective dose may be achieve by the multiple immunizations whether or not each individual immunization comprises an effective dose. Dosing regimens are further discussed below.

In some embodiments, vaccines are stored in a sealed vial, ampule, or similar container.

Vaccines may, in some embodiments, be lyophilized into a dried form, which may allow ease in transportation and storage. In some such embodiments, vaccines are dissolved or suspended in a solution or buffer before administration.

In some embodiments, vaccines are mixed together with other therapeutic agents (such as other vaccines or antigens associated with other diseases). In some embodiments, the other therapeutic agents do not diminish effectiveness of the vaccine composition against cholera.

Vaccines may be formulated for any of a variety of routes of administration as discussed further below. For example, vaccines may be formulated as a spray for intranasal inhalation, nose drops, swabs for tonsils, etc. Vaccines may be formulated for oral delivery in the form of capsules, tablets, gels, thin films, liquid suspensions and/or elixirs, etc.

D. Routes of Administration and Dosing

It will be appreciated that suitable routes of administration and dosing regimens may vary depending on various factors such as age, weight, height, sex, general medical condition, previous medical history, etc of the subject. Certain routes of administration (for example, intranasal and oral) and/or dosing regimens may be particularly suitable for use in humans.

In some embodiments of the invention, the composition is administered intranasally. Intranasal administration of the provided vaccine compositions may induce mucosal immune response and/or a serum antibody response. Intranasal administration may be advantageous over other routes of administration in certain aspects. For example, intranasal administration may obviate side effects such as nausea, stomach upset, or other digestive disturbance, that may accompany oral routes of administration. Compositions provided in the present disclosure may be administered intranasally, for example, via administration of a mist, aerosol, spray, and/or liquid droplets into the nose.

In some embodiments, compositions are designed such that exposure to the lungs is limited. For example, aerosols may be designed in such a way that the aerosol particle size limits the administration of the vaccine to the nasal pharynx, and not the oral pharynx or lungs. In such embodiments, large particles would stay in the nose, and few and/or very small particles would reach the alveoli in the lungs. The study of droplet size and point of delivery has been well studied for intranasal administration of medication. This expertise can be adapted to ensure that large droplets of the composition stay localized to the nasal mucosa. As another example, liquid droplets may be designed such that the volume of liquid delivered is below that which can flow or be aspirated down into the lungs.

In some embodiments of the invention, the composition is administered orally by ingestion. Vaccines may be formulated as, for example, capsules, tablets, gels, thin films, liquid suspensions and/or elixirs, etc.

Routes of administration also include subcutaneous, intradermal, and intramuscular.

Routes of administration that may be particularly suitable for use in non-human animals include intragastric (via the stomach) and intraperitoneal. Intragastric administration may comprise, for example, oral gavage, which involves insertion of a tube containing the composition into the oesophagus and delivering the composition directly into the stomach using a syringe or pump. In some embodiments of the invention, the composition is administered intraperitoneally, across the peritoneum. Intraperitoneal administration may comprise, for example, injection of the composition into the peritoneal space using a syringe applied to the abdomen.

Dosing regimens may comprise a single immunization or multiple immunizations. For example, vaccines may be given as a primary immunization followed by one or more boosters. Boosters may be delivered via the same and/or different route as the primary immunization. Boosters are generally administered after a time period after the primary immunization or the previously administered booster. For example a booster can be given about two weeks or more after a primary immunization, and/or a second booster can be given about two weeks or more after the first boosters. Boosters may be given repeatedly at time periods, for example, about two weeks or greater throughout up through the entirety of a subject's life. Boosters may be spaced, for example, about two weeks, about three weeks, about four weeks, about one month, about two months, about three months, about four months, about five months, about six months, about seven months, about eight months, about nine months, about ten months, about eleven months, about one year, about one and a half years, about two years, about two and a half years, about three years, about three and a half years, about four years, about four and a half years, about five years, or more after a primary immunization or after a previous booster.

Doses generally each comprise between about 1 pg and about 500 mg of protein content of OMVs per kg of body weight. In some embodiments, doses range between about 2 pg/kg and about 100 mg/kg. Doses may range, for example, between about 10 pg/kg to about 10 mg/kg, between about 100 pg/kg to about 1 mg/kg, between about 1 μg/kg to about 500 μg/kg, between about 5 μg/kg to about 100 μg/kg, between about 10 μg/kg to about 50 μg/kg, etc.

E. Immunity

Provided are methods comprising administering a composition containing OMVs obtained from *V. cholerae*. In some embodiments of the invention, such methods confer immunity to the individual to which the composition is administered. In other embodiments of the invention, immunity is conferred to one or more offspring of the individual to which the composition is administered. For example, the individual being administered the composition can be a pregnant female, whose future or current offspring benefit from immune protection. Such immunity may be passed from mother to child, for example, through breastmilk and/or through blood exchanged between from mother and fetus via the placenta.

In some embodiments of the invention, the immunity that is conferred is protective against *V. cholerae*. In some embodiments of the invention, the conferred immunity is also protective against other pathogens such as *Shigellae, Salmonella enterica, Campylobacter jejuni, Helicobacter pylori, E. coli* (such, as for example, enterotoxigenic *E. coli* (ETEC)), rotavirus, etc. Protection against pathogens other than *V. cholerae* can be mediated, for example, by the inclusion of heterologous proteins or other gene products in the OMVs, as discussed in the section below.

F. Heterologous Gene Products

Provided in the present invention are vaccine compositions comprising *V. cholerae* OMVs that are loaded with heterologous gene products, and methods of administering such compositions.

In some embodiments of the invention, OMVs contain foreign proteins or other gene products not normally expressed by wild type strains of *V. cholerae*. Genes encoding such proteins can be introduced into existing wild type or mutant strains of *V. cholerae* by methods known in the art, for example, using genetic elements such as transposable elements, viruses, plasmids, and etc. In some embodiments of the invention, such heterologous proteins are constitutively expressed by the bacterial strain after introduction of the foreign genetic element. In some embodiments of the invention, the heterologous proteins are expressed by the bacterial strain after induction. For example, heterologous genes inserted into a plasmid and under the control of a lac repressor system may be introduced into *V. cholerae*. Inducers such IPTG (isopropyl beta-D-thiogalactoside) may be used to induce expression of proteins or gene products encoded by the heterologous genes.

In some embodiments, heterologous gene products are targeted to certain organelles and/or spaces within the cell. For example, heterologous gene products may be targeted to the periplasm and/or to a membrane (e.g., the outer membrane). Targeting to certain organelles and/or spaces such as the periplasm and membranes may facilitate the heterologous gene products being present in OMVs produced by the bacterium.

In some embodiments, heterologous gene products are secreted and become attached to the surfaces of OMVs.

In certain embodiments of the invention, the heterologous gene product is derived from another bacterial species such as *E. coli* and expressed in *V. cholerae* bacteria. It may be desirable, for example, to load *V. cholerae* OMVs with immunogenic gene products from other pathogens that infect via the gastrointestinal tract, such as *Shigellae* (such as, for example, *Shigella dysenteriae, Shigella flexneri, Shigella boydii, Shigella sonnei*,), *Salmonellae* (such as, for example, *S. enterica*), *Campylobacter jejuni, Helicobacter pylori*, rotavirus, *E. coli* (including subtypes such as enterotoxigenic *E. coli* (ETEC), enteropathogenic *E. coli* (EPEC), enterohemorrhagic *E. coli* (EHEC), enteroinvasive *E. coli* (EIEC), and enteroaggregative *E. coli* (EAggEC), and/or combinations thereof. Vaccine compositions comprising such gene products may confer immunity to diseases mediated by such pathogens. In some embodiments of the invention, compositions comprise gene products from more than one pathogenic species and may confer immunity to more than one infectious disease. For example, the heterologous gene product may be a gene product derived from ETEC. OMVs derived from *V. cholerae* that also contain such heterologous gene products may contain immunogenic gene products from both *V. cholerae* and from ETEC, and may confer immunity to both cholera and ETEC-mediated diseases. Other combinations of heterologous gene products may be used with methods provided in the present disclosure. For example, OMVs loaded with rotavirus, ETEC, and *V. cholerae* gene products may be obtained from *V. cholerae* bacteria manipulated to express rotavirus and ETEC gene products. Such OMVs may confer immunity to all three pathogens.

The heterologous gene product may be any kind of gene product whose expression can be achieved in *V. cholerae*. For example, the heterologous gene product may be cholera toxin B subunit. The gene may be constitutively expressed and/or inducible. In some such embodiments, chlorotoxin B subunit protein accumulates to high amounts in the periplasm and may also accumulate in high amounts in OMVs.

In some embodiments of the invention, the heterologous protein is a tag, such as a fluorescent protein. Such proteins can facilitate tracking and/or visualization of molecules. Examples of fluorescent proteins include, but are not limited to, green fluorescent protein (GFP) from the jellyfish *Aequorea victoria*; mutant versions of GFP that fluoresce different colors (such as BFP, blue fluorescent protein; YFP, yellow fluorescent protein; and CFP, cyan fluorescent protein); dsRed fluorescent protein (dsRed2FP); eqFP611, a red fluorescent protein isolated from *Entacmaea quadricolor*; AmCyan1, a cyan fluorescent protein isolated from *Anemonia majano*, and originally named amFP486; Azami Green, a bright fluorescent protein isolated from *Galaxeidae*; ZSGREEN™, a fluorescent protein isolated from *Zoanthus*; etc.

In some embodiments of the invention, the heterologous gene product is an enhanced version of a fluorescent protein, such as enhanced GFP (EGFP), enhanced BFP (EBFP), enhanced YFP (EYFP), enhanced CFP (ECFP), etc. It will be understood by one of ordinary skill in the art that other mutants of fluorescent proteins, such as those that enhance fluorescence, affect the wavelength of emitted light, and/or affect stability of the protein, can also be used with methods provided in the present disclosure. Fusion proteins involving fluorescent proteins may also be used with provided methods.

In some embodiments of the invention, the heterologous gene product is a gene product that enhances stability of OMVs. In some embodiments of the invention, the heterologous gene product is a gene product that enhances uptake of OMVs into the body of the individual being administered the composition comprising *V. cholerae* OMVs. In some embodiments of the invention, the heterologous gene product is a gene product that enhances immune response to OMVs.

In some embodiments of the invention, the heterologous gene product interferes with the expression of one or more genes in the host *V. cholerae* bacterial strain and/or in the subject to which the vaccine is administered. For example, the heterologous gene product could be an agent capable of altering gene expression in cells (such as, for example cells of the subject). Such an agent may, for example, bind to surface receptors and/or enter into cells.

In some embodiments of the invention, the heterologous gene product is an RNA molecule that interferes with gene expression. In some embodiments, the heterologous gene product is an agent that mediates RNA interference (RNAi), the sequence-specific silencing of gene expression by double-stranded RNA molecules. Such agents include, but are not limited to, short interfering RNA (siRNA), short hairpin RNA (shRNA), micro RNA (miRNA) etc. In some embodiments, the heterologous gene product is another RNA molecule that interferes with gene expression, such as an antisense RNA molecule or a ribozyme In some embodiments of the invention, the heterologous gene product is a dominant negative form of a protein, which blocks or prevents activity of the endogenous form.

In some embodiments of the invention, the heterologous gene product is not in a naturally occurring form. The heterologous gene product can be a protein fused to part or all of another protein. For example, it may be desirable to secrete a particular heterologous protein. The heterologous protein may be fused to another protein that is secreted, or fused to the secretion signal of another protein, such that the fusion protein is also secreted. In other embodiments of the invention, the heterologous protein is fused to tag, such as an affinity tag, an epitope tag, a fluorescent tag, etc. Examples of fluorescent tags include GFP and other fluorescent proteins mentioned above. Affinity tags can facilitate the purification or solubilization of fusion proteins. Examples of affinity tags include maltose binding protein (MBP), glutathione-5-transferase (GST), thioredoxin, polyhistidine (also known as hexa histidine, 6×His, and by the trademarked name HIS-TAG®), etc. Examples of epitope tags, which facilitate recognition by antibodies, include c-myc, FLAG (FLAG octapeptides), HA (hemagglutinin), etc.

In some embodiments of the invention, the heterologous gene product is a product of a genetically manipulated gene. As mentioned above, the heterologous gene product can be a dominant negative form of a protein. As another example, the heterologous gene product can be the product of a gene that has been manipulated such that it is regulated differently than the endogenous version of the gene is. The gene can be under the control of a promoter that confers a different pattern of expression than the endogenous promoter does (e.g., a different tissue distribution, a different spatial distribution, and/or a different temporal expression). In some embodiments of the invention, the gene is under the control of a promoter or other regulatory genetic element that allows inducible gene expression, such as the lac repressor system mentioned herein.

In some embodiments of the invention, the heterologous gene product is loaded into OMVs. Such loading can occur, for example, when the heterologous gene product contains a secretion signal. The secretion signal may be present in the endogenous form of the gene product, may be present due to fusion to a protein or protein fragment containing a secretion signal, or may be present due to another genetic manipulation that results in inclusion of one or more secretion signal sequences. Thus, OMVs prepared from strains manipulated to express heterologous proteins can contain the heterologous proteins.

In some embodiments of the invention, the heterologous gene product is a gene product normally present in *V. cholerae*, but altered in some way. Alteration of a gene product may be accomplished, for example, by mutation of the gene encoding it. Such mutations may alter one or more characteristics of the gene product that affects, for example, the stability, uptake, and/or immunogenicity of the OMVs. Other alterations of endogenous gene products may involve placing the endogenous gene or a mutated version of the endogenous gene under the control of a regulatory element that alters expression of the gene. Such a modification to the regulation of the gene may result in, for example, increased or decreased gene product, inducible expression of the gene, and/or altered temporal and spatial distribution of the gene product. For example, it may be desirable to increase the expression of a gene product if increased expression of the gene product would enhance the immunogenicity of the OMVs or decrease the dose of the vaccine composition required to achieve the effective dose. Such OMVs may, for example, confer immunity and protection from more than one strain of *V. cholerae.*

In some embodiments of the invention, more than one type of heterologous gene product is expressed by *V. cholerae* and loaded into OMVs obtained from *V. cholerae.*

EXAMPLES

The following examples describe some of the preferred modes of making and practicing the present invention. However, it should be understood that these examples are for illustrative purposes only and are not meant to limit the scope of the invention.

Bacterial Strains

In the following examples, the bacterial strains used were as follows. *V. cholerae* E7946 and O395 were used as wild-type (wt) strains. E7946 is a clinical isolate from the 7$^{th}$ cholera pandemic, and is of the O1 serogroup, El Tor biotype and Ogawa serotype. O395 is a clinical isolate from the 6$^{th}$ pandemic and is of the O1 serogroup, classical biotype and Ogawa serotype. Strain AC108 is a derivative of O395 harboring a TnphoA insertion in the tcp operon. The site of TnphoA insertion is undetermined, but has resulted in a translation fusion of phoA to a secreted protein such that PhoA is exported to the periplasm, generating active alkaline phosphatase activity in the periplasm. Unless stated otherwise, bacteria were grown in Luria-Bertani broth (LB) at 37° C. with aeration. Supplements were used in the following final concentrations: streptomycin (Sm, 100 μg/ml), ampicillin (Ap, 100 μg/ml or 50 μg/ml when in combination with Sm).

Example 1

Isolation of Outer Membrane Vesicles (OMVs)

To isolate OMVs produced by E7946, bacterial cultures (1 liter of LB broth, Fisher Scientific) were inoculated with 10 mL of LB over-night (O/N) stationary phase culture and grown to late exponential-phase for 8 hours. Cells were pelleted by centrifugation (6000 rpm, 15 minutes, 4° C.) using a Sorvall centrifuge RC5B and a GS-3 rotor. The supernatant was filtered consecutively through 0.45 μm and 0.22 μm pore size filters (Corning, 430512 and 430186) to give complete removal of remaining bacteria. To confirm the absence of viable bacteria, 1 mL of the filtrate was plated on an LB agar plate and incubated overnight at 37° C. and examined for colonies. No colonies were observed. In order to prevent possible protein degradation, protease inhibitor (Roche, Complete EDTA-free protease inhibitor cocktail, 1 tablet per 1 liter of filtrate) was added to the filtrate and stored at 4° C. Within the next five days OMVs were purified from the filtrate by ultracentrifugation (4 hours, 140,000×g, 4° C.) using a Beckman L8-80M ultracentrifuge and a SW32Ti or 50.2Ti rotor, washed once with 10 mL phosphate-buffered saline (PBS) and finally resuspended in 625 μL of PBS. The protein concentration was determined by the Modified Lowry Protein Assay Kit (Pierce) and adjusted to 2.5 μg/μL using PBS and stored at −80° C.

To induce expression of the Tcp-PhoA fusion in AC108, 5 mL of an LB O/N stationary phase culture was diluted in 500 mL mildly acidic LB broth (0.5% Tryptone, 0.25% Yeast Extract, 20.2% NaCl, pH 6.5) and grown at 30° C. for 8 hours. OMVs of this culture were harvested as described above.

Example 2

Stability of OMVs

To evaluate the stability of proteins within purified OMVs, 25 μL of OMVs were incubated at −80, +25 or +37° C. After 4 weeks, we 5 μl of each OMV sample were mixed with 20 μL Laemmli-buffer. Then 2 and 5 μL of each sample were loaded on a SDS-PAGE gel and the proteins were electrophoretically separated. Protein bands were stained with IMPERIAL™ Protein Stain (Pierce).

As shown in FIG. 1, the proteins bands from all three samples are comparable in pattern and intensity, indicating that the proteins were stable under all conditions tested for 4 weeks. Thus, a cold-chain is unlikely to be required for shipping and administration of a *V. cholerae* OMV vaccine.

Example 3

OMV Density Gradient Fractionation

The following experiment was conducted to examine differences between OMVs of different densities.

OMVs were isolated as described in Example 1, but resuspended in 50 mM Hepes pH 7.5 with 45% Optiprep (Sigma). 150 μL were transferred to the bottom of a SW41Ti tube (Beckman) and overlayed with Hepes/Optiprep layers as follows: 2.7 mL of 35% Optiprep in 50 mM Hepes, 2.7 mL of 30% Optiprep in 50 mM Hepes, 2 mL of 25% Optiprep in 50 mM Hepes, 2 mL of 20% Optiprep in 50 mM Hepes H, 1 mL of 15% Optiprep in 50 mM Hepes and 1 mL of 10% Optiprep in 50 mM Hepes. Gradients were centrifuged (3 h, 180,000× g, 4° C.) using a Beckman L8-80M ultracentrifuge and an SW41Ti rotor. 21 fractions of equal volume were sequentially removed from the top and 10 mL of 50 mM Hepes pH 7.5 was added to each. OMVs in each fraction were harvested by ultracentrifugation (3 h, 180,000×g, 4° C.) using a Beckman L8-80M ultracentrifuge and a SW41Ti rotor, resuspended in 20 μL 50 mM Hepes pH 7.5 and analyzed by SDS-PAGE.

Figure 2:
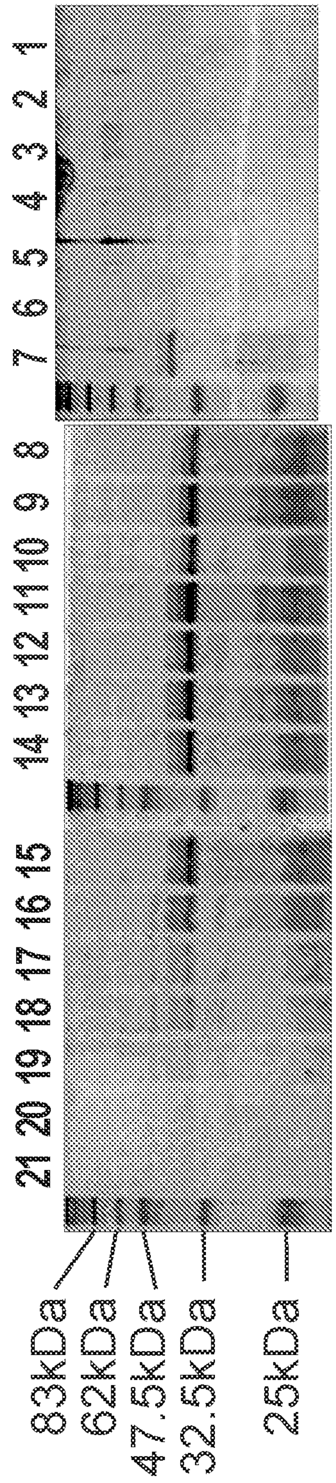
FIG. 2 depicts the results from an experiment examining the protein content of various density gradient fractions of OMVs isolated from a wild type *V. cholerae* strain (E7946). Fractions are shown in reverse order (21-1) from left to right, corresponding to most dense to least dense fractions. (Fraction 1 was the first fraction removed from the top of the sucrose gradient, whereas fraction 21 was the bottom fraction.) Molecular weight markers are shown in the leftmost lanes of each of the three panels. Corresponding sizes to the molecular weight markers are indicated on the far left. 5 microliters of each fraction were electrophoretically separated by SDS-PAGE and stained with IMPERIAL™ Protein Stain (Pierce).

FIG. 2 shows a typical pattern of the protein content of the fractions from OMVs isolated from wt. Fraction 1 was the first fraction removed from the top, whereas fraction 21 was the bottom fraction. 5 μL of each fraction was loaded. The results show that OMVs of differing density differ in their protein content.

Example 4

Purification of Outer Membrane (OM) Proteins

OM was purified from *V. cholerae* E7946, as well as from isogenic strains harboring deletions in genes for outer membrane porins OmpT and OmpU, and in the gene for ToxR, which is a transcriptional regulator of ompU and ompT. The strains were grown overnight in 50 mL LB broth to stationary phase. Cells were harvested using an Allegra X-15R centrifuge (Beckman) and a SX4750A rotor (15 minutes, 4,750 rpm, 4° C.), washed once in 15 mL 10 mM Hepes pH 7.5 and resuspended in 1.5 mL 10 mM Hepes pH 7.5 with protease inhibitor (Roche, Complete EDTA-free protease inhibitor cocktail, 1 tablet per 2 mL of resuspended cells). Cells were disrupted using a Mini Beadbeater (Biospec) and 0.5 μL of 0.1 mm silica beads (Biospec).

Unbroken cells were removed by centrifugation in an Eppendorf centrifuge 5415R (1 minutes, 13,000 rpm, 4° C.) and the supernatant containing the OM proteins was transferred into a new tube and centrifuged again (30 minutes, 13,000 rpm, 4° C.). The pellet was resuspended in 0.8 μL 10 mM Hepes pH 7.5/1% sarcosyl and incubated for 30 minutes. After centrifugation (30 minutes, 13,000 rpm, 4° C.), the pellet was washed once with 1 mL 10 mM Hepes pH 7.5 and finally resuspended in 50 μL 10 mM Hepes pH 7.5.

Example 5

Comparison of OM and OMV Proteins

In order to determine if the protein content of the OMVs reflect in part that of the OM, the protein profiles of the OM and OMVs from wt E7946, ΔompT, ΔompU and a ΔtoxR strain were compared. OM proteins or OMVs were isolated as described in Examples 4 and 1 respectively. OMVs were fractionated by density gradient as described in Example 3. OMV fraction 16 of an Optiprep gradient was used to compare the OMV against the OM proteins. 5 μL of each OMV sample and 3 μL of each OM sample was loaded on a SDS-PAGE gel and electrophoretically separated. Protein bands were stained with IMPERIAL™ Protein Stain (Pierce).

Figure 3:
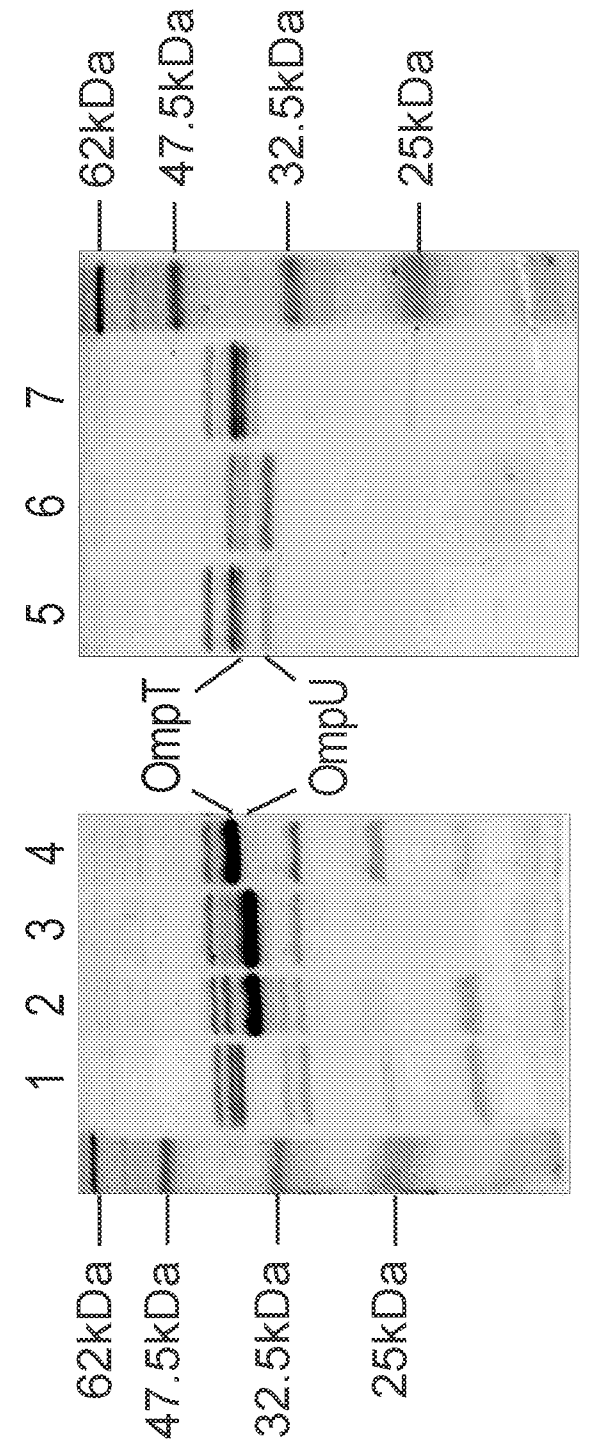
FIG. 3 shows the results of an experiment comparing outer membrane (OM) proteins with that of OMVs derived from wild type *V. cholerae* and mutant *V. cholera* strains with deletions (Δ) of genes encoding OM proteins such that the resulting strains have altered OM protein content. Lanes: 1) OM from E7946ΔompU, 2) OM from E7946ΔompT, 3) OM from wt E7946, 4) OM from E7946ΔtoxR, 5) fraction 16 from density gradient purification of OMV from wt E7946, 6) fraction 16 from density gradient purification of OMV from E7946ΔompT, and 7) fraction 16 from density gradient purification of OMV from E7946ΔtoxR. Samples were separated by SDS-PAGE and stained with IMPERIAL™ Protein Stain (Pierce). The positions of outer membrane porins OmpT and OmpU are shown in the middle.

The results are shown in FIG. 3. Some of the changes in the protein content of the OM directly correspond to changes in the protein profile of the OMVs. Since ToxR is a known positive regulator of OmpU, the toxR mutant lacks the OmpU protein in the OM and in the OMV sample.

These findings indicate that the isolated vesicles are indeed derived from the OM and that their protein profiles can be modified by mutagenesis.

Example 6

Expressing a Heterologous Protein in *V. Cholerae* that Partitions into OMVs To test whether a foreign (heterologous) protein can be expressed in *V. cholerae* such that the foreign protein partitions into OMVs, OMVs were prepared from strain AC108. This O395 derivative contains a translational fusion of the *E. coli* alkaline phosphatase lacking its signal sequence (PhoA, 47 kDa) to an unknown secreted protein in the tcp operon. OMVs were prepared as described in Example 1. As a control, whole cell lysates (WCL) were prepared from the same culture as the OMVs. 1 mL of culture was centrifuged in an Eppendorf centrifuge 5415D (5 minutes, 5,000 rpm, room-temperature [RT]), washed once with PBS and resuspended in 0.5 μl Laemmli buffer. In order to achieve complete lysis and inactivation of proteases, the sample was boiled for 30 min. The Mini-Protean 3 System (Biorad) was used for SDS-PAGE. The XCELL II™ Blot Module (Invitrogen) was used to transfer protein to nitrocellulose membrane. The membrane was blocked with 5% skim milk dissolved in PBS-T (PBS buffer with 0.1% Tween) at 4° C. overnight on a rocker. The primary antibody (anti-PhoA from rabbit; courtesy A. Wright, Tufts University School of Medicine) was diluted 1:10,000 in 5% skim milk dissolved in PBS-T, incubated at room temperature for 4 h on a rocker, and washed 3 times for 5 min with PBS-T. The secondary antibody (horseradish peroxidase conjugated anti-rabbit IgG from goat; GE Healthcare UK Limited) was diluted 1:5,000 in PBST, applied to the membrane, and incubated at RT for 2 h at RT on a rocker. The membrane was washed 3 times for 5 min with PBS-T, and chemiluminescent detection was performed using the ECL Plus Western Blotting Detection System (GE Healthcare UK Limited) and exposure to X-ray film (Kodak).

BALB/c mice (Charles River Laboratories) were immunized intranasally with OMVs of strain AC108 as described in Example 7.

Figure 4:
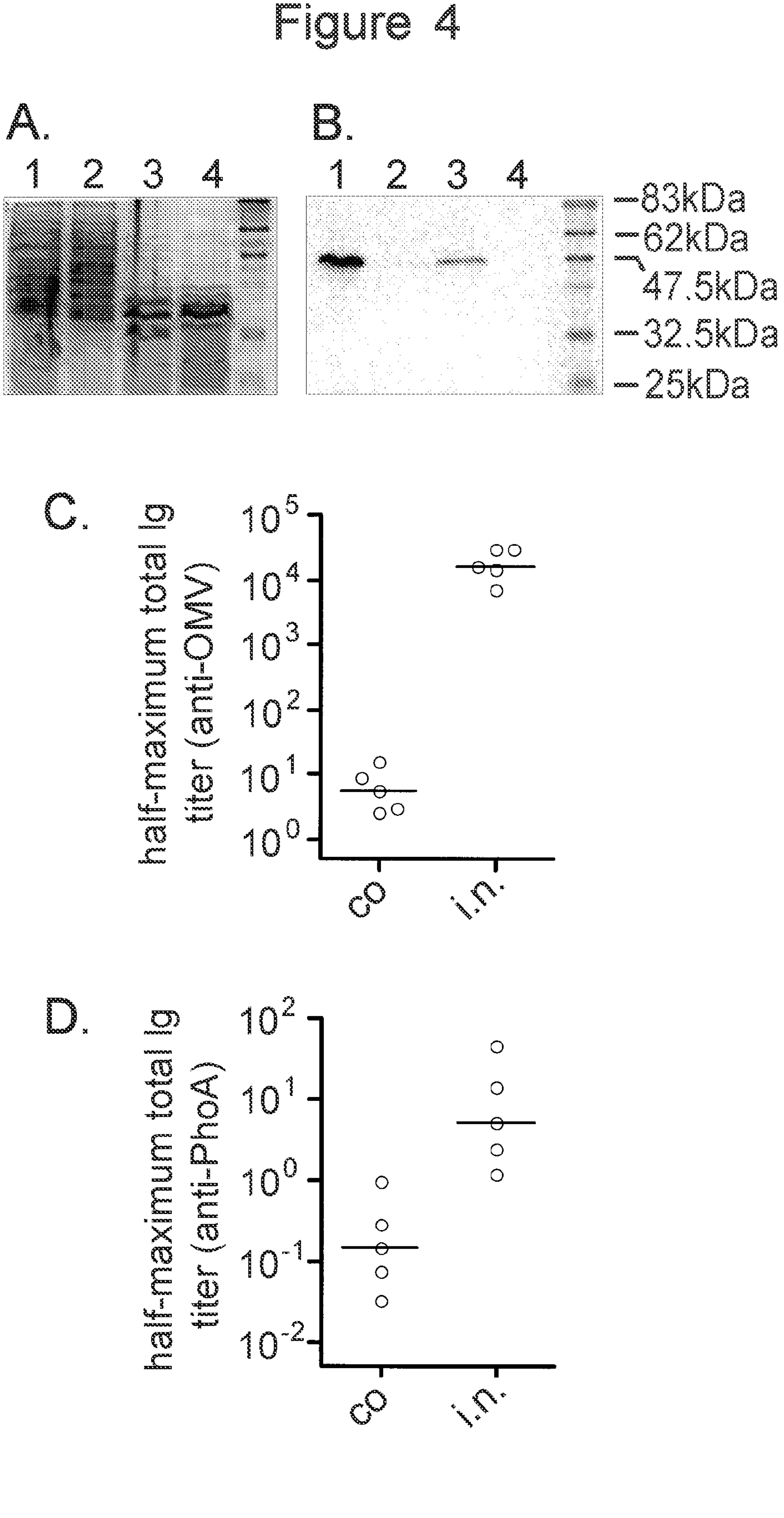
FIG. 4 depicts the results of experiments testing whether a foreign (heterologous) protein, PhoA, can be loaded into *V. cholerae* OMVs and whether such heterologous protein can be antigenic. *V. cholera* strain AC 108 is a derivative of the O1 serogroup strain O395 that expresses the PhoA heterologous protein from *E. coli*. Panel A shows total protein from whole cell lysates (WCL) of AC108 (lane 1) or wt E7946 (lane 2) and OMVs derived from AC108 (lane 3) or wt E7946 (lane 4) that have been separated by SDS-PAGE and stained with IMPERIAL™ Protein Stain (Pierce). Panel B shows a Western blot of a duplicate gel stained with anti-PhoA antibody. Panels C and D show results of experiments to examine antigenicity of the heterologous protein in the context of the *V. cholerae* OMV vaccine. The half-maximum total anti-OMV (panel C) or anti-PhoA (panel D) immunoglobulin (Ig) titers in serum of mice intranasally (i.n.) vaccinated with OMVs derived from AC108 are shown. The non-vaccinated control group is indicated by 'co.' Each circle represents the half-maximum total immunoglobulin titer from one mouse. Horizontal bars indicate the median of each data set.

The results are shown in FIG. 4. PhoA is readily detected in WCL and in OMVs of strain AC108, but not in WCL of O395 or OMVs of E7946. Immunization with OMVs of strain AC108 induced a specific immune response against PhoA. This experiment demonstrates that OMVs can be loaded with a heterologous protein that is known to localize to the periplasm of Gram-negative bacteria and that such heterologous proteins can serve as antigens.

Example 7

Vaccination with OMVs

This Example demonstrates intranasal vaccination with OMVs obtained from *V. cholerae.*

BALB/c mice (Charles River Laboratories) were used in all experiments. Mice were anesthetized by inhalation of 2.5% isoflurane gas prior to all immunizations. 7-week-old female mice were immunized at days 0, 14 and 28 with OMVs via the intraperitoneal (i.p.), intragastric (i.g.) or intranasal (i.n.) routes using the following concentrations: i.p. −1 μg in 50 μl PBS for the initial immunization at day 0 and 0.25 μg in 50 μl PBS at day 14 and 28; i.g. −25 μg in 100 μl PBS for all immunizations; i.n. −25 μg in 10 μl PBS (5 μl per nare) for all immunizations. Nonvaccinated control mice were housed in parallel with the vaccinated mice for the duration of the experiment. Blood was collected by lateral tail vein nick at days 0, 14, 28 and 38, as well 4 to 8 days after the first challenge, and by cardiac puncture 4 to 8 days after the second challenge.

Western Blot Analysis

The antibody response of the vaccinated and control mice was analyzed by Western blot using the Mini Trans-Blot Cell system (Biorad). The collected blood was allowed to clot at room temperature for 30 min after which serum was isolated by removing the blood clot by centrifugation in an Eppendorf centrifuge 5415D (15 min, 3,000 rpm, room temperature). The supernatant was removed and diluted 3-fold in PBS. After adding sodium azide to a final concentration of 0.05% the serum was stored at −80° C.

OMV and OM were purified as above. OMV and OM proteins were separated by SDS-PAGE as describe in Examples 1 and 4 and were transferred onto a nitrocellulose membrane (Invitrogen). The membrane was blocked by incubation in 10% skim milk in TBS-TT (20 ml 1 M Tris pH 7.5, 50 ml 5 M NaCl, 2 ml Triton, 500 μl Tween in 1 liter) for 2 h at room temperature. The membrane was washed twice in TBS-TT and once in TBS (20 ml 1 M Tris pH 7.5, 30 ml 5 M NaCl in 1 liter) for 10 min each.

For use as the primary antibody, the mouse serum was diluted 1:500 in 10% skim milk in TBS-TT. The diluted serum was added to a membrane and incubated at 4° C. overnight on a rocker. The membrane was then washed as described above. After washing, the membrane was incubated for 1 h in the secondary antibody solution using horseradish peroxidase conjugated anti-mouse IgG from sheep (GE Healthcare UK Limited) in 10% skim milk in TBS. The membrane was washed four times in TBS-TT for 10 min each wash. Chemiluminescent detection was performed by using the ECL plus Western Blotting Detection System (GE Healthcare UK Limited) and exposure to X-ray film (Kodak).

Figure 5:
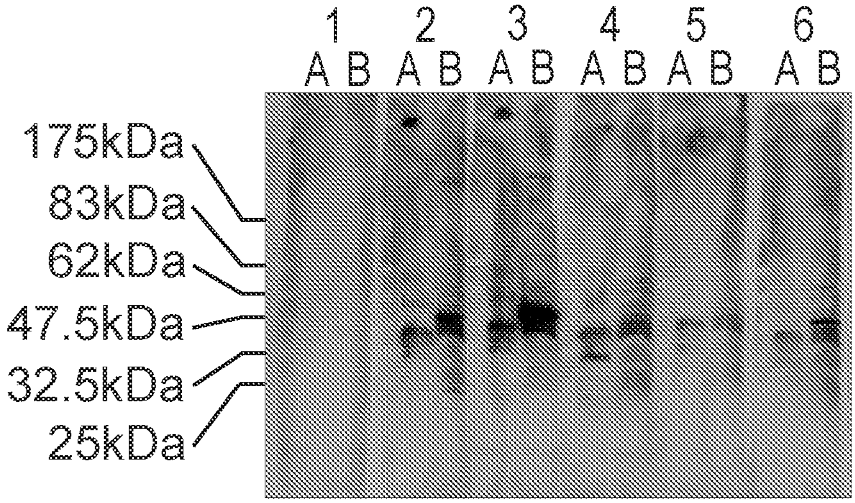
FIG. 5 depicts the results of an experiment testing the immune response of vaccinated mice against *V. cholerae* proteins. Shown is a Western blot in which OMV and OM proteins are detected using sera from vaccinated mice, indicating that the sera contained antibodies against *V. cholerae* proteins. Six membranes labeled 1-6 are shown, each hybridized with the serum from an individual mouse. In each membrane, lanes A and B correspond to 7 μg OMV protein and 7 μg OM protein, respectively. Sizes of molecular weight markers are designated on the left. Membrane 1 was blotted with serum from an unvaccinated control mouse. Membranes 2-6 were blotted with sera from mice vaccinated with OMVs by the following routes: 2) intraperitoneally (i.p.), 3) i.p., 4) intragastrically (i.g.), 5) i.g., and 6) intranasally (i.n.).

The results from a representative Western blot utilizing sera from the bleeds at day 28 are shown in FIG. 5. Each serum was tested against OMV and OM protein. The results show that all vaccinated mice have developed an immune response against *V. cholerae* proteins, since sera from these mice are capable of detecting proteins in both samples, whereas the serum from the control mouse does not.

Enzyme-Linked ImmunoSorbent Assay (ELISA)

Concentrations of immunoglobulins in fecal pellets of mice immunized with different amounts of OMVs were determined. Three to five freshly voided fecal pellets were vacuum-dried for 10 min before their dry weight was recorded. Immunoglobulins were extracted from fecal pellets by adding 1 mL of extraction buffer (PBS, 0.01% sodium azide, 5% fetal calf serum, 1 tablet Complete EDTA-free protease inhibitor cocktail (Roche) per mL) per 100 mg of feces and vortexing the samples for 15 min at 4° C. Solid material was separated by centrifugation (2 minutes, 13,000 g) and the supernatants were stored at −80° C. using 1 mL extraction buffer per 100 mg feces. Levels of IgA and IgG1 isotype antibodies to OMVs were determined by ELISA using 96-well ELISA Microplates (BD Falcon). Plates were coated by incubation with OMVs (5 μg/ml in PBS) at 4° C. for two days. To generate standard curves for each isotype, plates were coated in triplicate with 2-fold dilutions of the appropriate purified mouse Ig isotype standard (IgA and IgG1, BD Biosciences) starting at 1 μg/ml in PBS. After washing four times with 0.05% Tween in PBS (PBS-T), nonspecific binding sites were blocked with 10% heat-inactivated fetal calf serum in PBS (PBS-F) for 1 hour at room temperature. Starting at 1:400 in PBS-F, appropriate 5-fold dilutions of the test samples were applied on the OMV coated wells in triplicate, whereas PBS-F was used for the wells coated with isotype standards. Plates were incubated for 1 hour at room temperature and washed four times with PBS-F. The plates were then incubated for 1 hour at room temperature with the appropriate alkaline phosphatase-conjugated affinity-purified goat antibodies against mouse IgA (α-chain specific, Southern Biotech) or IgG1 (γ1-chain specific, Southern Biotech). After four washes with PBS-F, plates were developed using the BluePhos® Microwell Phosphatase Substrate System and Stop Solution (KPL) according to the manufacturer's instructions. Optical densities were read at 620 nm with a Synergy HT plate reader (Biotek Inc.). Titers were calculated using values from the appropriate dilutions of test samples and a log-log regression calculated from at least four dilutions of the isotype standards.

Figure 9:
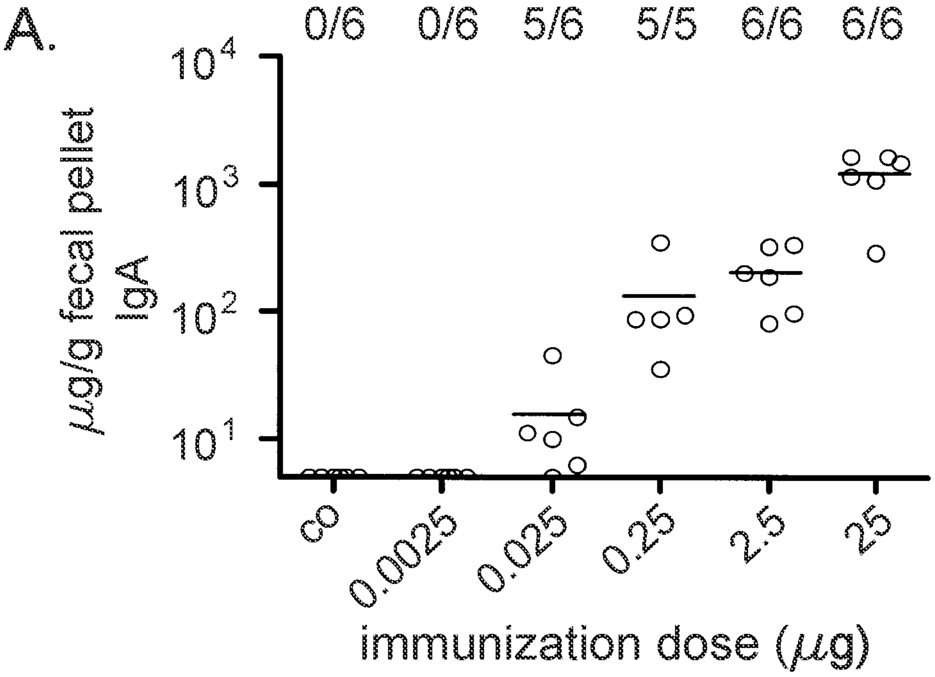
FIG. 9 depicts anti-OMV titers of IgA (panel A) and IgG1 (panel B) extracted from fecal pellets collected from adult mice vaccinated i.n. with different amounts of OMVs. The OMV dose per immunization is given for each group on the x-axis. The non-vaccinated control group is indicated by 'co.' Each circle represents the immunoglobulin titer of one mouse. Horizontal bars indicate the median of each data set. The number of samples with detectable immunoglobulin titers/total number of samples tested is shown above each data set. Samples with no detectable immunoglobulin titers were set to the respective limit of detection, which were 5 μg/g fecal pellet in the case of IgA and 0.05 μg/g fecal pellet in the case of IgG1, respectively.
Figure 9:
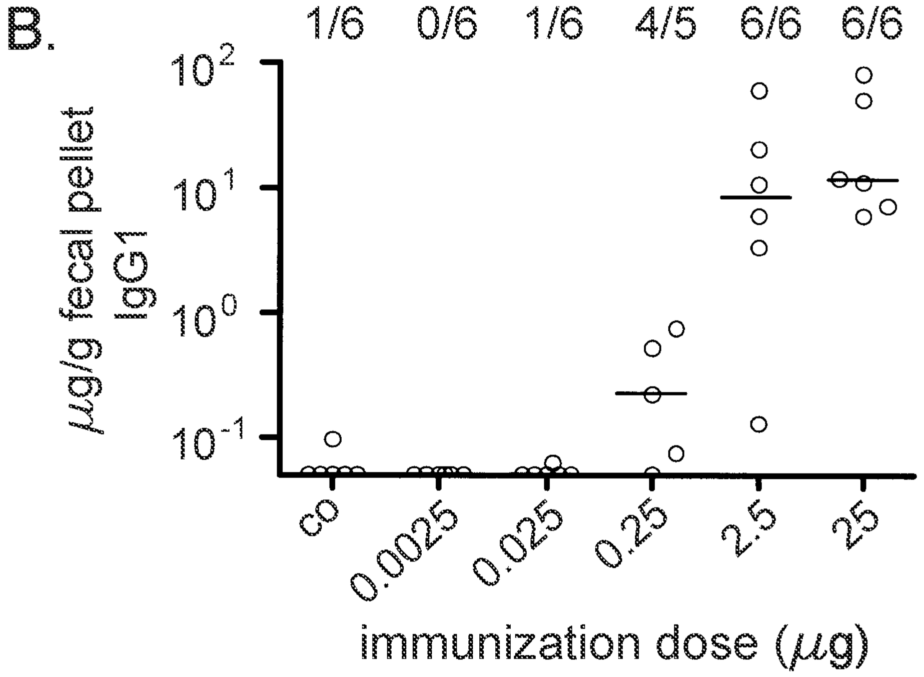

Results are shown in FIG. 9. An induced IgA and IgG1 response in the intestinal tract of the majority of our mice immunized intranasally could be detected.

Half-maximum total Ig titers (total Ig is defined as IgA +, IgG and + IgM) were determined by ELISA for the sera samples of mice immunized intranasally with OMVs of AC108 as described above, except that half-maximum total Ig titers against PhoA and total OMVs were determined separately. Thus, ELISA plates were coated either with OMVs derived from AC108 (as described above) or purified PhoA (Sigma). Since PhoA cross-reacts with the BluePhos® Microwell Phosphatase Substrate, we used horseradish peroxidase-conjugated affinity-purified goat Igs against mouse (IgM+IgG+IgA, H+L, Southern Biotech) as a secondary Ig in combination with the TMB 2-Component Microwell Peroxidase Substrate Kit and TMB BlueSTOP™ Solution (KPL) according to the manufacturer manual in these assays. At least four five-fold dilutions starting at 1:4 up to 1:400 were used to calculate the half-maximum total Ig titers. Half-maximum titers were calculated by plotting the log of the reciprocal dilutions of mouse sera against the resulting absorbances, which has a sigmoidal relationship, to determine the reciprocal that gave half of the maximum optical density.

Results are shown in FIG. 4, Panelsle C and D. Mice immunized intranasally with OMVs of AC108 induced a small but significant specific immune response against PhoA.

Example 8

*V. cholerae* Challenge of Infant Mice (pups) from Vaccinated and Non-Vaccinated Dams This Example demonstrates that mice from vaccinated dams received immune protection against *V. cholerae*.

Determining the $ID_{50}$ for E7946 in pups. To first determine the $ID_{50}$, the dose at which 50% of pups are typically infected, for strain E7946 in pups of naïve dams, E7946 was streaked for pure colonies on LB plus Sm agar plates and grown overnight at 37° C. Approximately 60 colonies were resuspended in LB broth and adjusted to an optical density of 1 (equivalent to approximately $2\times10^9$ CFU/ml). Serial dilutions at the following ratios were prepared; 1:10 ('D1'=$2\times10^8$ CFU/ml; $1\times10^7$ CFU/mouse), 1:50 ('D2'=$4\times10^6$ CFU/ml; $2\times10^5$ CFU/mouse), 1:100 ('D3'=$4\times10^5$ CFU/ml; $2\times10^4$ CFU/mouse), 1:1,000 ('D4'=$4\times10^4$ CFU/ml; $2\times10^3$ CFU/mouse), 1:10,000 ('D5'=$4\times10^3$ CFU/ml; $2\times10^2$ CFU/mouse), and 1:100,000 ('D6'=$4\times10^2$ CFU/ml; $2\times10^1$ CFU/mouse).

Four to six-day-old pups were separated from naïve dams for 1 h, anesthetized by inhalation of 2.5% isoflurane gas, and then inoculated i.g. by oral gavage with 50 μl of the appropriate serial dilution (described above). In parallel, the CFU/ml for the dilution series was determined by quantifying the D5 and D6 dilutions on LB plus streptomycin plates with overnight incubation at 37° C., and back calculating for the lower dilutions (D1-D4). The inoculated pups were kept either with or away from their dams for 24 h. Pups of naïve dams were kept away from their dams as a control for the $ID_{50}$ determination of strain E7946 only. This control would evaluate how the $ID_{50}$ is affected by the presence or absence of the dam and her milk; all subsequent challenge experiments were conducted with the pups placed back with the mothers. The mice were sacrificed by humane measures consistent with recommendations of the Panel on Euthanasia of the American Veterinary Medical Association. The small intestine from each pup was removed by dissection and mechanically homogenized. Dilutions of the homogenized small intestine were made in PBS, and plated for colony counts on LB plus streptomycin plates. All adult mice were housed with food and water ad libitum and under the care of full time staff and in accordance with the rules of the Department of Lab Animal Medicine at the host institutions.

Figure 6:
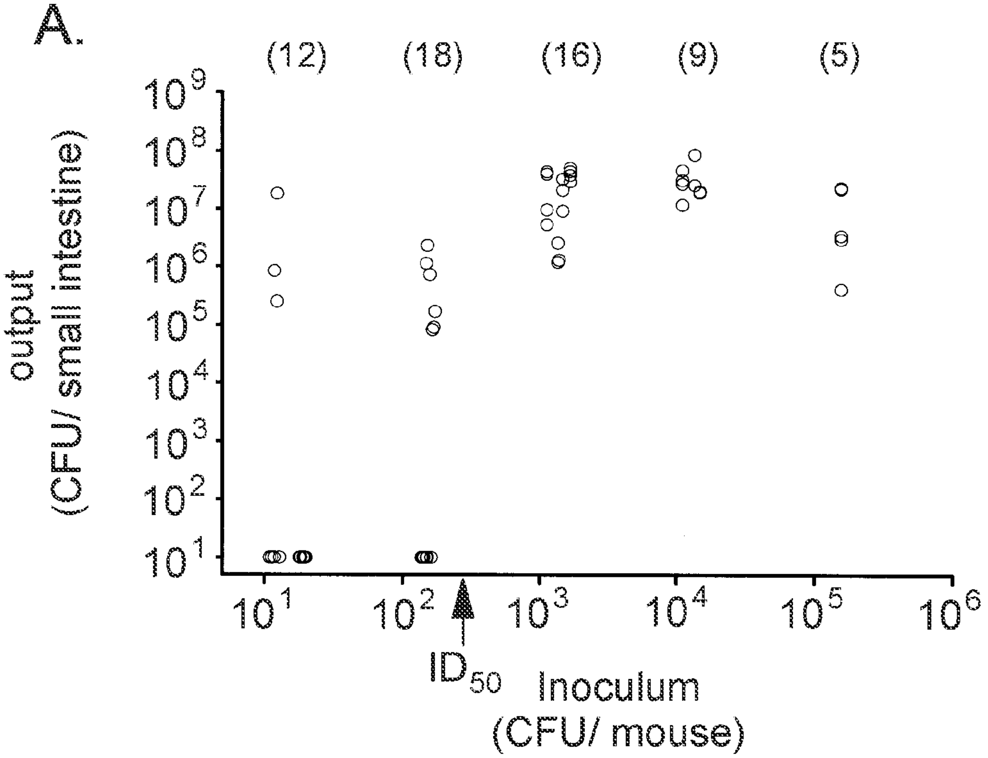
FIG. 6 depicts the results of an experiment to determine the dose at which 50% of pups are typically infected ($ID_{50}$) for strain E7946 in pups from naïve dams. The amount of bacteria in the inoculum is given on the x-axis, whereas the number of bacteria colonized (recovered from dissected small intestine) 24 hours after infection is given on the y-axis. Panel A shows results from infant mice given back to their dams after i.g. infection. Panel B shows results for mice kept separate after i.g. infection. $ID_{50}$ values in each experiment are shown at the bottom by the arrow. The number of pups in each group is given in parentheses at the top of each panel above the corresponding data points at the top of each panel.
Figure 6:
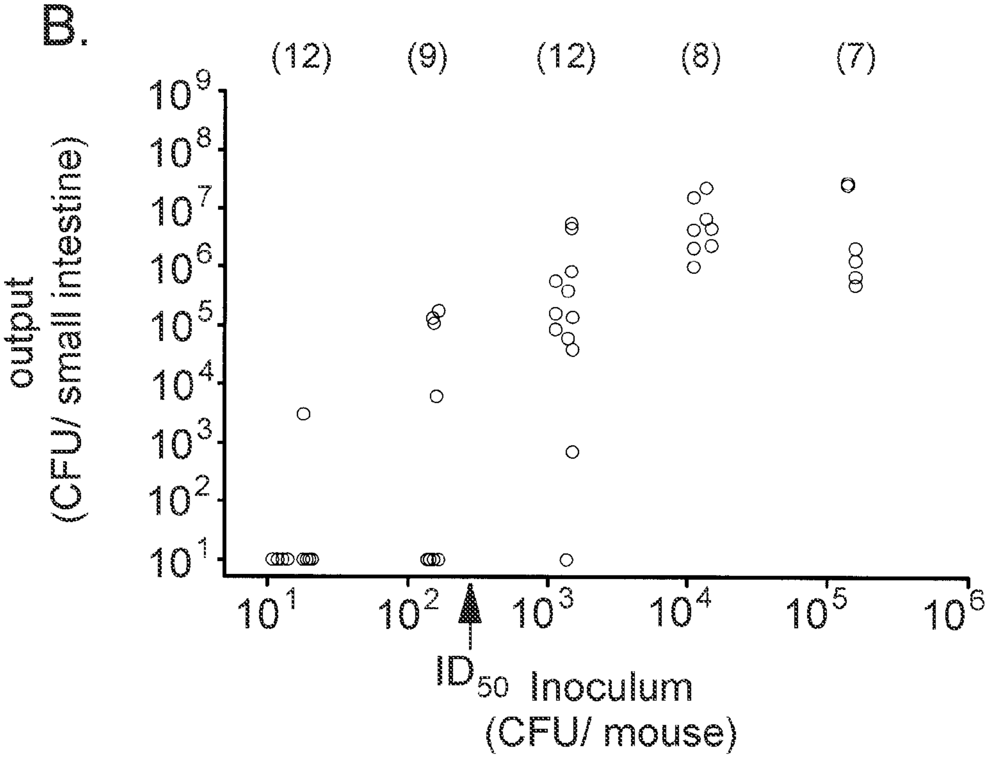

The results of the $ID_{50}$ determination infections are shown in FIG. 6, panels A and B. The amount of bacteria in the inoculum is given on the x-axis, whereas the number of bacteria colonized is given on the y-axis. Panel A summarizes the results for infant mice given back to their dams after infection, panel B shows the data for mice kept separated after infection. The graphically determined $ID_{50}$ in both experiments is approximately 200 CFU per mouse, indicated by an arrow in both graphs. The similar $ID_{50}$s in both experiments demonstrate that the naïve dam and/or her milk do not seem to interfere with colonization. If anything, it appears to enhance colonization at the lower doses, since in Panel A (infant mice given back to dams) the maximal colonization of about $10^7$ CFU is reached with a D4 inoculation mix.

Short Term Protection Study

Having determined the $ID_{50}$ for strain E7946 with naïve dams (approximately 200 CFU/mouse, which is approximately equal to a 50 μL i.g. inoculation with D5), pups of control and vaccinated dams were challenged with *V. cholerae* at approximately 10 (D4) and 100 (D3) times the $ID_{50}$. The short term protection challenge experiments were conducted on pups obtained by mating the vaccinated mice 13 days after the third vaccination (described above). Thus, the pups were born approximately 37 days and challenged approximately 42 days after the third and final vaccination of the dams. After i.g. inoculation the pups were placed back in the presence of their respective dam. After 24 h, the pups were sacrificed and the small intestine of each pup was harvested and analyzed as described above.

Figure 7:
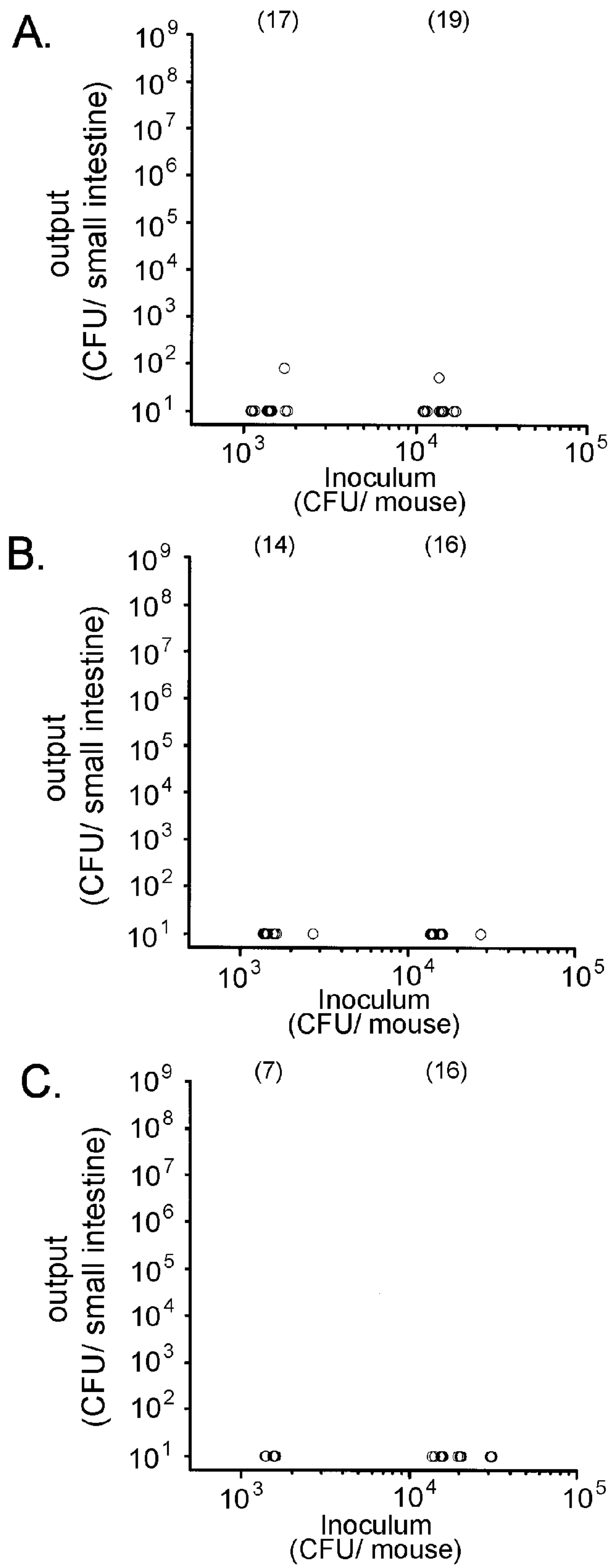
FIG. 7 depicts the results from a short term protection experiment. Pups from vaccinated dams were challenged i.g. with the inoculum amounts given on the x-axis. The number of bacteria colonized is given on the y-axis. Panels A, B, and C show results from pups from dams vaccinated i.p., i.g., and i.n., respectively. The number of pups in each group is given in parentheses above the corresponding data points at the top of each panel.

Results are shown in panels A-C of FIG. 7. Panel A shows the results for infant mice from i.p. vaccinated dams, panel B for infant mice from i.g. vaccinated dams, and panel C for infant mice from i.n. vaccinated dams. For all pups from i.g. and i.n. vaccinated dams the colonization was below the detection limit of 10 CFU per mouse small intestine. In some pups from i.p. vaccinated dams colonization with *V. cholerae* was detectable, but at least 10.000-fold lower than in the infection of naïve animals (compare with FIG. 6). Therefore, all pups from vaccinated dams demonstrated robust short term protection.

Long Term Protection Study

To measure long term protection, pups of control and vaccinated dams were challenged with higher doses of *V. cholerae* at approximately 100 (D3) and 1000 (D2) times the $ID_{50}$. The long term protection challenge experiments were conducted on pups obtained by mating the vaccinated mice 62 days after the third vaccination (described above).

Figure 8:
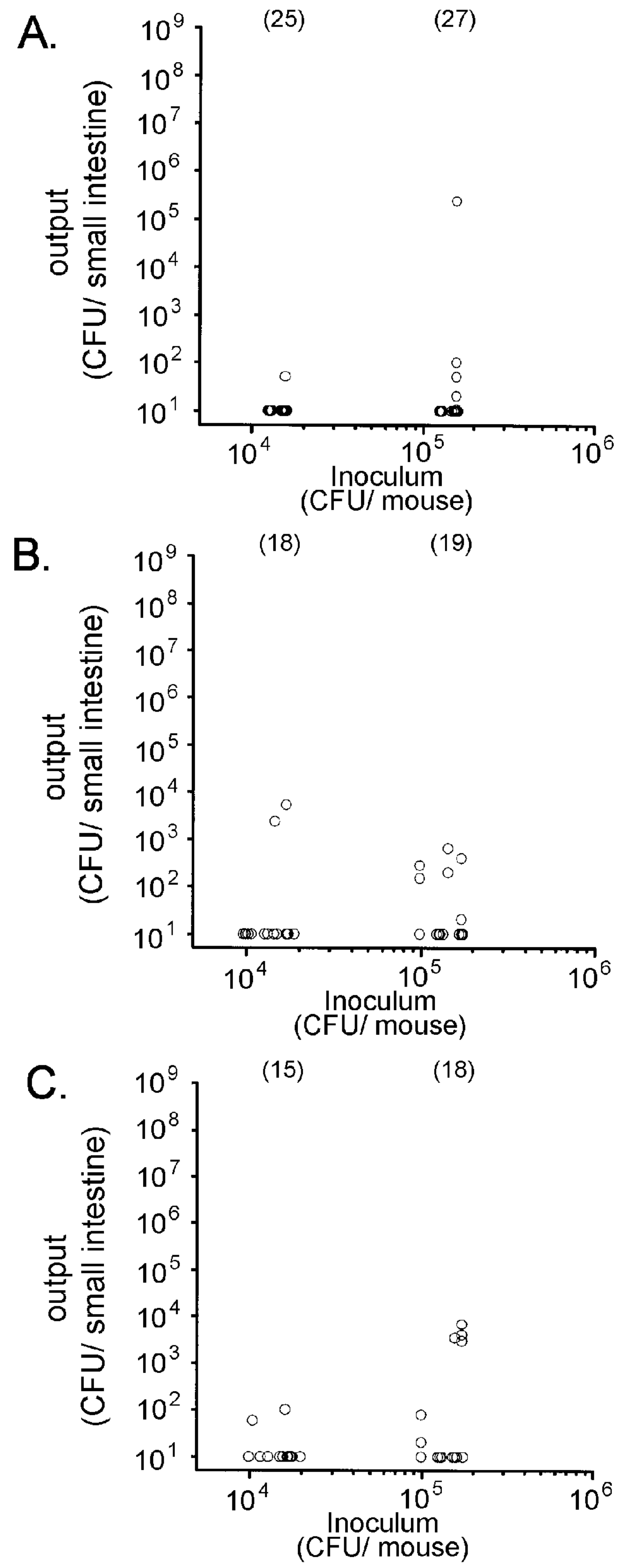
FIG. 8 depicts the results of a long term protection experiment. Pups from vaccinated dams were challenged i.g. with the inoculum amounts given on the x-axis. The number of bacteria colonized in the small intestine is given on the y-axis. Panels A, B, and C show results from pups from dams vaccinated i.p., i.g., and i.n., respectively. The number of pups in each group is given in parentheses above the corresponding data points at the top of each panel.

Thus, the pups were born approximately 84 days and challenged approximately 89 days after the third and final vaccination of the dams. The pups were placed back in the presence of their respective dam. After 24 h, the pups were sacrificed and the small intestine of each pup was harvested and analyzed as described above. Results are shown in FIG. 8, panels A-C. Panel A shows the results for infant mice from i.p. vaccinated dams, panel B for infant mice from i.g. vaccinated dams, and panel C for infant mice from i.n. vaccinated dams. For all pups from i.p. vaccinated dams the colonization was below the detection limit of 10 CFU per mouse. In some pups from i.g. and i.n. vaccinated dams colonization with *V. cholerae* was detectable, but at least 1.000-fold lower than in the infection with naïve animals (compare with FIG. 6). Therefore, all pups from vaccinated dams demonstrated robust long term protection.

Example 9

Dose Effects of *V. cholerae* OMVs

To examine dosing ranges that confer protection against *V. cholerae*, challenge experiments were carried out on adult mice vaccinated intranasally, or on pups who mothers were vaccinated intranasally with different doses of *V. cholerae* OMVs.

Intranasal vaccination and challenge experiments were carried out as described in Example 8. In this Example, mice were immunized intranasally using different amounts of OMVs equivalent to about 0.0025 μg, about 0.025 μg, about 0.25 μg, about 2.5 μg, or about 25 μg OMVs per immunization.

IgA and IgG1 titers in fecal pellets from immunized adult mice were measured as described in Example 7. As shown in FIG. 9, IgA was detected in pellets from mice immunized with as little as 0.025 μg OMVs per immunization, and IgG1 was detected in pellets from mice immunized with as little as 0.25 μg per immunization.

Figure 10:
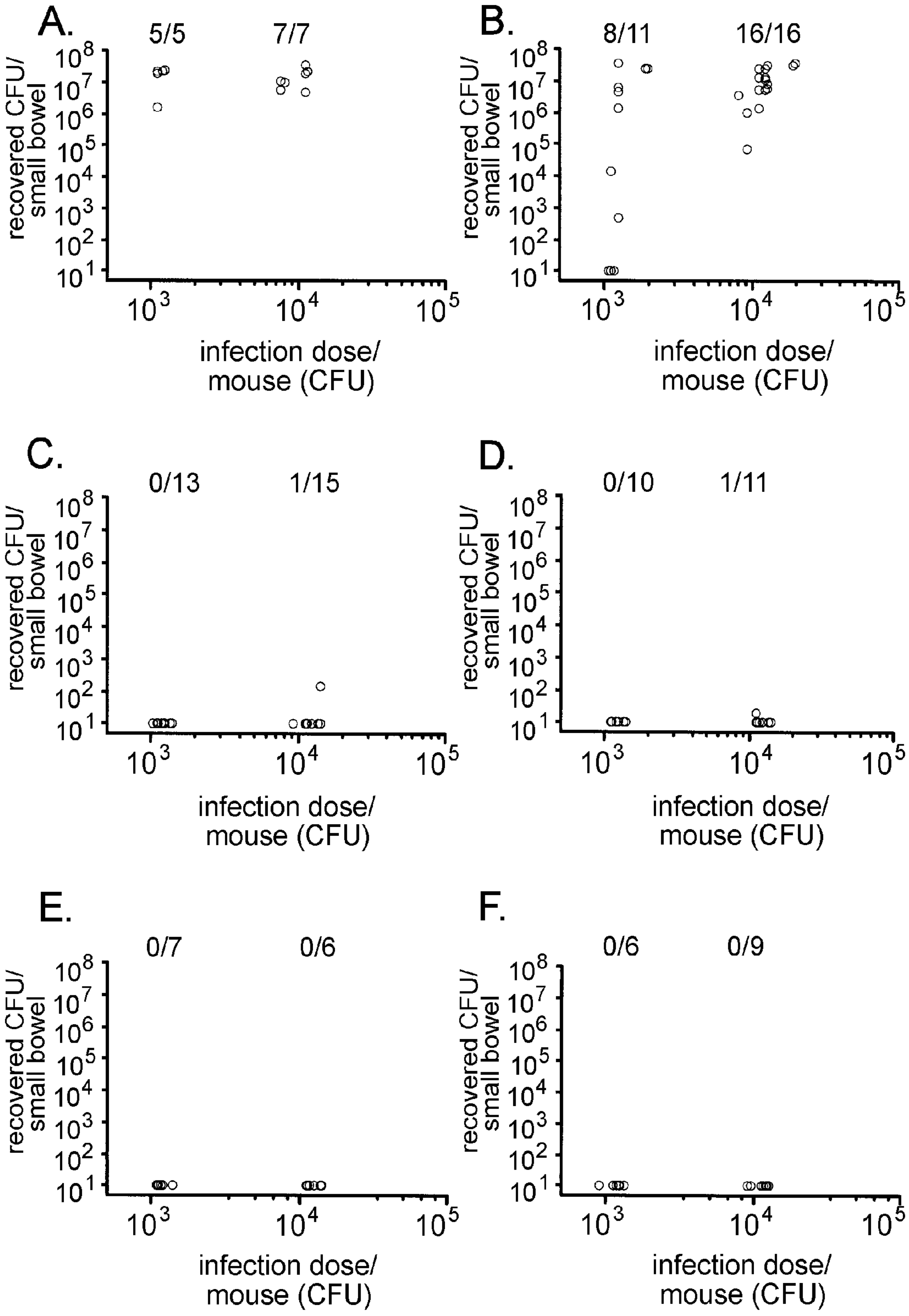
FIG. 10 depicts results of experiments determining the protection against colonization with *V. cholerae* after vaccination with different amounts of OMVs. Pups of vaccinated dams were challenged i.g. with the inoculum amounts given on the x-axis. The number of bacteria colonized in the small intestine is given on the y-axis. Results are shown for neonatal mice born by dams of the non-vaccinated control group (A) and groups immunized in with various OMV amounts equivalent to 0.0025 μg (B), 0.025 μg (C), 0.25 μg (D), 2.5 μg (E) and 25 μg (F) OMV protein per immunization. Each circle represents the number of colony forming units (CFU) from the small intestine of one neonatal mouse. If no bacteria could be recovered, then the CFUs were set to the limit of detection of 10 CFU/small intestine. The number of mice with detectable colonization/total number of challenged mice is shown above the respective inoculum.

Protection in pups was analyzed by dissecting small bowels from pups and measuring the number of colony forming units (CFU) recovered from the dissected small bowels. In such analyses, decreased numbers of CFUs as compared to control samples indicate protective immunity. As depicted in FIG. 10, pups from dams vaccinated with as little as about 0.025 μg OMVs per immunization showed protective immunity.

Other Embodiments

Other embodiments of the invention will be apparent to those skilled in the art from a consideration of the specification or practice of the invention disclosed herein. It is intended that the specification and examples be considered as exemplary only, with the true scope of the invention being indicated by the following claims.

What is claimed is:

1. A vaccine composition comprising isolated outer membrane vesicles obtained from *Vibrio cholerae*, which outer membrane vesicles comprise a lipid bilayer containing integral or surface associated outer membrane (OM) proteins, phospholipids and lipopolysaccharides of a *Vibrio cholera* strain that is either:

(a) the combination of O1 serogroup having the E1 Tor biotype and the Ogawa serotype; or (b) the combination of O1 serogroup having the classical biotype and having the Ogawa serotype;

which strain carries a deletion of:

(c) one or more outer membrane proteins selected from the group consisting of ompU and ompT; or (d) a toxR regulator of outer membrane proteins, wherein the outer membrane vesicles have an altered protein content as compared with outer membrane vesicles shed from wild type *Vibrio cholerae*.

2. The vaccine composition of claim 1, wherein the composition is suitable for intranasal administration.

3. The vaccine composition of claim 1, further comprising one or more gene products not normally expressed in wild type strains of *Vibrio cholerae*.

4. The vaccine composition of claim 3, wherein the one or more gene products include one or more gene products from at least one pathogen other than *Vibrio cholerae*.

5. The vaccine composition of claim 4, wherein the at least one pathogen is selected from the group consisting of *Shigellae, Salmonellae enterica, Campylobacter jejuni, Helicobacter pylori, E. coli*, rotavirus, and combinations thereof.

6. The vaccine composition of claim 5, wherein the at least one pathogen is or comprises *E. coli* selected from the group consisting of enterotoxigenic *E. coli* (ETEC), enteropathogenic *E. coli* (EPEC), enterohemorrhagic *E. coli* (EHEC), enteroinvasive *E. coli* (EIEC), enteroaggregative *E. coli* (EAggEc), and combinations thereof.

7. The vaccine composition of claim 5, wherein the at least one pathogen is or comprises are *Shigellae* selected from the group consisting of *Shigella dysenteriae, Shigella flexneri, Shigella boydii, Shigella sonnei*, and combinations thereof.

8. A method comprising a step of administering to an individual an effective amount of a composition comprising outer membrane vesicles obtained from *Vibrio cholera* as recited in claim 1.

9. The method of claim 8, wherein immunity from cholera is conferred to the individual.

10. The method of claim 8, wherein the composition further comprises one or more gene products not normally expressed in wild type strains of *Vibrio cholerae*.

11. The method of claim 8, wherein immunity from cholera is conferred to one or more offspring of the individual.

12. The method of claim 11, wherein the one or more gene products are gene products from pathogens other than *Vibrio cholerae*.

13. The method of claim 12, wherein the gene product are gene products from pathogens selected from the group consisting of *Shigellae, Salmonellae enterica, Campylobacter jejuni, Helicobacter pylori, E. coli*, rotavirus, and combinations thereof.

14. The method of claim 13, wherein the pathogens are *E. coli* selected from the group consisting of enterotoxigenic *E. coli* (ETEC), enteropathogenic *E. coli* (EPEC), enterohemorrhagic *E. coli* (EHEC), enteroinvasive *E. coli* (EIEC), enteroaggregative *E. coli* (EAggEC), and combinations thereof.

15. The method of claim 13, wherein the pathogens are *Shigellae* selected from the group consisting of *Shigella dysenteriae, Shigella flexneri, Shigella boydii, Shigella sonnei*, and combinations thereof.

16. The method of claim 8, wherein the route of administration is selected from the group consisting of intranasal, oral, subcutaneous, intradermal, intramuscular, intraperitoneal, and intragastric.

17. The method of claim 16, wherein the route of administration is intranasal.

18. The method of claim 16, wherein the route of administration is oral.

19. A method comprising steps of (a) providing *Vibrio cholerae* cells grown in culture of a *Vibrio cholera* strain that is either:

(i) the combination of O1 serogroup having the E1 Tor biotype and the Ogawa serotype; or (ii) the combination of O1 serogroup, having the classical biotype and having the Ogawa serotype, return which strain carries a deletion of:

(iii) one or more outer membrane proteins selected from the group consisting of ompU and ompT; or (iv) of a toxR regulator of outer membrane proteins, (b) preparing outer membrane vesicles from said *Vibrio cholerae* cells, which outer membrane vesicles have an altered protein content as compared with outer membrane vesicles shed from wild type *Vibrio cholera*; and (c) formulating a vaccine composition as recited in claim 1, that comprises said outer membrane vesicles.

20. The method of claim 19, wherein the *Vibrio cholerae* cells are of a strain selected from the group consisting of E7946 and O395.

21. The method of claim 19, wherein the vaccine composition is suitable for intranasal administration.

22. The method of claim 19, wherein the outer membrane vesicles contain one or more gene products not normally expressed in wild type strains of *Vibrio cholerae*.

23. The method of claim 19, wherein the one or more gene products are gene products from pathogenic organisms other than *Vibrio cholerae*.

24. The method of claim 23, wherein the one or more gene products are gene products from pathogenic organisms selected from the group consisting of *Shigellae, Salmonellae enterica, Campylobacter jejuni, Helicobacter pylori, E. coli*, rotavirus, and combinations thereof.

25. The method of claim 24, wherein the pathogens are *E. coli* selected from the group consisting of enterotoxigenic *E. coli* (ETEC), enteropathogenic *E. coli* (EPEC), enterohemorrhagic *E. coli* (EHEC), enteroinvasive *E. coli* (EIEC), enteroaggregative *E. coli* (EAggEc), and combinations thereof.

26. The method of claim 24, wherein the pathogens are *Shigellae* selected from the group consisting of *Shigella dysenteriae, Shigella flexneri, Shigella boydii, Shigella sonnei*, and combinations thereof.

* * * * *

UNITED STATES PATENT AND TRADEMARK OFFICE

CERTIFICATE OF CORRECTION

PATENT NO. : 8,642,046 B2
APPLICATION NO. : 12/681951
DATED : February 4, 2014
INVENTOR(S) : Camilli et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 397 days.

Signed and Sealed this
Twenty-second Day of September, 2015

Michelle K. Lee

Michelle K. Lee
*Director of the United States Patent and Trademark Office*